US008658382B2

(12) United States Patent
Park et al.

(10) Patent No.: US 8,658,382 B2
(45) Date of Patent: Feb. 25, 2014

(54) PROTEINS WITH PTERIDINE GLYCOSYLTRANSFERASE ACTIVITY AND ANALYSIS METHOD USING THE SAME

(75) Inventors: Young-Shik Park, Gimhae-si (KR); Jin Han, Busan (KR)

(73) Assignee: Inje University Industry-Academic Cooperation Foundation, Gimhae-si (KR)

( * ) Notice: Subject to any disclaimer, the term of this patent is extended or adjusted under 35 U.S.C. 154(b) by 487 days.

(21) Appl. No.: 12/936,328

(22) PCT Filed: Mar. 30, 2009

(86) PCT No.: PCT/KR2009/001591
§ 371 (c)(1),
(2), (4) Date: Nov. 2, 2010

(87) PCT Pub. No.: WO2009/145429
PCT Pub. Date: Dec. 3, 2009

(65) Prior Publication Data
US 2011/0059473 A1 Mar. 10, 2011

(30) Foreign Application Priority Data
Apr. 2, 2008 (KR) .................. 10-2008-0030804
Feb. 27, 2009 (KR) .................. 10-2009-0016695

(51) Int. Cl.
*G01N 31/00* (2006.01)
*G01N 33/53* (2006.01)

(52) U.S. Cl.
USPC ........... 435/7.21; 435/7.1; 436/501; 436/518; 424/9.1; 424/520; 422/430; 530/300; 530/350

(58) Field of Classification Search
None
See application file for complete search history.

(56) References Cited

PUBLICATIONS

Choi et al. (FEBS Letter, 2001, vol. 502, pp. 73-78).*
Castillo, S., et al. "Quantitative Analysis of Tetrahydrobiopterin, Dihydrobiopterin and Biopterin in Plasma Using Reverse Phase Hplc, Electrochemical and Fluorescence Detection". AAPS National Biotechnology Conference. Abstract 2008.
Choi, Y.K., et al. "Chemical structure of 1-O-(L-erythro-biopterin-2'-yl)-α-glucose isolated from a cyanobacterium Synechococcus sp. PCC 7942". Pteridines. 2001, vol. 12, No. 3, pp. 121-125.
Choi, Y.K., et al. "Molecular cloning and disruption of a novel gene encoding UDP-glucose:tetrahydrobiopterin α-glucosyltransferase in the cyanobacterium Synechococcus sp. PCC 7942". FEBS Letters. 2001, vol. 502, pp. 73-78.
Chung, H.J., et al. "Purification and characterization of UDP-glucose:tetrahydrobiopterin glucosyltransferase from Synechococcus sp. PCC 7942". Biochimica et Biophysica Acta. 2000, vol. 1524, pp. 183-188.
Danfors, T., MD, et al. "Tetrahydrobiopterin in the treatment of children with autistic disorder: a double-blind placebo-controlled crossover study". Journal of Clinical Psychopharmacology. 2005, vol. 25, No. 5, pp. 485-489.
Duch, D.S., et al. "Biosynthesis and function of tetrahydrobiopterin". J. Nutr. Biochem., 1991, vol. 2, pp. 411-423.
Fukushima, T. et al. "Analysis of reduced forms of biopterin in biological tissues and fluids". Analytical Biochemistry. 1980, vol. 102, pp. 176-188.
Hyland, K. "Estimation of tetrahydro, dihydro and fully oxidised pterins by high-performance liquid chromatography using sequential electrochemical and fluorometric detection". Journal of Chromatography. 1985, vol. 343, pp. 35-41.
Ichinose, H., et al. "Hereditary progressive dystonia with marked diurnal fluctuation caused by mutations in the GTP cyclohydrolase I gene". Nature Genetics. 1994, vol. 8, pp. 236-242.
Kaneko, Y.S., et al. "Determination of tetrahydrobiopterin in murine locus coeruleus by HPLC with fluorescence detection". Brain Research Protocols. 2001, vol. 8, pp. 25-31.
Lunte, C.E., et al. "The determination of pterins in biological samples by liquid chromatography/electrochemistry". Analytical Biochemistry. 1983, vol. 129, pp. 377-386.
Moens, A.L., et al. "Tetrahydrobiopterin and cardiovascular disease". Arteriosclerosis, Thrombosis, and Vascular Biology. 2006, vol. 26, pp. 2439-2444.
Nichol, C.A., et al. "Biosynthesis and metabolism of tetrahydrobiopterin and molybdopterin". Ann. Rev. Biochem. 1985, vol. 54, pp. 729-764.
Richardson, M.A., et al. "Analysis of plasma biopterin levels in psychiatric disorders suggests a common BH4 deficit in schizophrenia and schizoaffective disorder". Neurochem Res. 2007, vol. 32, pp. 107-113.
Schallreuter, K.U., et al. "In vivo evidence for compromised phenylalanine metabolism in vitiligo". Biochemical and Biophysical Research Communications. 1998, vol. 243, pp. 395-399.
Schmidt, T.S., et al. "Mechanisms for the role of tetrahydrobiopterin in endothelial function and vascular disease". Clinical Science. 2007, vol. 113, pp. 47-63.
Taylor, N.E., et al. "NO synthase uncoupling in the kidney of Dahl S rats: Role of dihydrobiopterin". Hypertension. 2006, vol. 48, pp. 1066-1071.
Thöny, B., et al. "Tetrahydrobiopterin biosynthesis, regeneration and functions". Biochem. J. 2000, vol. 347, pp. 1-16.
Tiemeier, H., et al. "Plasma pterins and folate in late life depression: The Rotterdam study". Psychiatry Research. 2006, vol. 145, pp. 199-206.

(Continued)

*Primary Examiner* — Lisa Cook
(74) *Attorney, Agent, or Firm* — Nath, Goldberg & Meyer; Joshua B. Goldberg

(57) ABSTRACT

The present invention relates to proteins with pteridine glycosyltransferase activity and an analysis method using the same. Since the proteins glycate tetrahydrobiopterin selectively through an enzyme reaction, the method enables quantitative analysis of tetrahydrobiopterin and oxides thereof at the same time or quantitative analysis of tetrabiopterin selectively.

6 Claims, 13 Drawing Sheets

(56) References Cited

PUBLICATIONS

Triglia, T., et al. "A procedure for in vitro amplification of DNA segments that lie outside the boundaries of known sequences". Nucleic Acids Research. 1988, vol. 16, No. 16, p. 8186.

Yada, T., et al. "Changes of asymmetric dimethylarginine, nitric oxide, tetrahydrobiopterin, and oxidative stress in patients with acute myocardial infarction by medical treatments". Clinical Hemorheology and Microcirculation. 2007, vol. 37, pp. 269-276.

* cited by examiner

SEQUENCE LISTING

<160> NUMBER OF SEQ ID NOS: 32

<210> SEQ ID NO 1
<211> LENGTH: 359
<212> TYPE: PRT
<213> ORGANISM: Synechococcus PCC7942

<400> SEQUENCE: 1

```
Met Thr Ala His Arg Phe Leu Phe Val Ser Thr Pro Val Gly Pro Leu
 1               5                  10                  15

Gly Ser Gly Arg Gly Gly Val Glu Leu Thr Leu Pro Asn Leu Ala
             20                  25                  30

Lys Ala Leu Thr Gln Arg Gly His Gln Val Ser Val Leu Ala Pro Ala
                 35                  40                  45

Gly Ser Val Leu Pro Asp Leu Pro Leu Glu Thr Val Pro Gly Thr Trp
         50                  55                  60

Gln Ser Thr Ala Gln Ser His Gly Arg Ala Thr Pro Ala Glu Ile Pro
 65                  70                  75                  80

Ala Glu Ser Val Leu Ala Arg Leu Trp Asp Arg Ala His Gln Gln
                 85                  90                  95

Ala Asp Phe Asp Leu Ile Leu Asn Phe Ala Tyr Asp Trp Leu Pro Leu
                100                 105                 110

Tyr Leu Thr Pro Phe Phe Lys Thr Pro Val Ala His Leu Ile Ser Met
            115                 120                 125

Gly Ser Leu Ser Glu Val Met Asp Gln Ala Ile Ala Thr Ser Leu Asp
        130                 135                 140

Arg Tyr Pro Gly Ser Ile Ala Val His Ser Leu Ala Gln Ala Ala Thr
145                 150                 155                 160

Phe Pro Phe Gly Asp Arg Cys Leu Cys Ile Gly Asn Ala Leu Asp Leu
                165                 170                 175

Ala Ala Tyr Gly Phe Asn Pro Glu Pro Glu Pro Val Leu Gly Trp Val
            180                 185                 190

Gly Arg Ile Ala Pro Glu Lys Gly Leu Glu Asp Ala Ile Gln Ala Ala
        195                 200                 205

Gln Gln Ala Gly Leu Pro Leu Arg Val Trp Gly Ala Leu Thr Glu Pro
    210                 215                 220

Asp Tyr Trp Gln Arg Leu Gln Gln Gln Phe Gly Asp Arg Ala Val Ser
225                 230                 235                 240

Tyr Gln Gly Phe Val Ser Thr Asp Glu Leu Gln Arg Gly Leu Gly Arg
                245                 250                 255

Cys Gln Gly Leu Leu Met Thr Pro Lys Trp Val Glu Ala Phe Gly Asn
            260                 265                 270

Val Ala Ile Glu Ala Leu Ala Cys Gly Leu Pro Val Ile Ala Tyr Ala
        275                 280                 285

Arg Gly Gly Pro Leu Glu Ile Ile Glu Gln Gly Lys Ser Gly Trp Leu
    290                 295                 300

Val Glu Pro Asp Gln Gln Ala Ala Leu Val Asn Ala Ile Gly Gln Leu
305                 310                 315                 320

Ser Ser Leu Asp Arg Ala Tyr Cys Arg Ala Gln Ala Glu Ala Arg Phe
                325                 330                 335

Ser Leu Ala Ala Met Gly Gln Arg Leu Glu Ala Trp Leu Leu Pro Leu
            340                 345                 350

Leu Ser Arg Ala Arg Gly Phe
        355
```

<210> SEQ ID NO 2
<211> LENGTH: 359
<212> TYPE: PRT
<213> ORGANISM: Spirulina platensis CY-7

<400> SEQUENCE: 2

```
Met Thr Pro Thr Ser Trp Lys Leu Leu Phe Ile Ser Thr Pro Val Gly
  1               5                   10                  15

Pro Leu Gly Ser Gly Leu Gly Gly Val Glu Leu Thr Leu Leu Asn
             20                  25                  30

Met Ala Lys Ala Leu Lys Ser Arg Gly His Asp Ile Thr Val Val Ala
             35                  40                  45

Pro Ser Gly Ser Val Leu Glu Ser Leu Ser Ile Glu Ile Pro Gly
         50                  55                  60

Glu Leu Gln Pro Ile Ala Gln Asn Gln Asp Arg Asp Ser Leu Ile Thr
 65                  70                  75                  80

Ile Pro Glu Asn Ser Val Leu Gly Asn Met Trp Glu Tyr Gly Arg Gln
                 85                  90                  95

Val Gln Thr Asn Tyr His Ala Ile Val Asn Phe Ala Phe Asp Trp Leu
            100                 105                 110

Pro Phe Tyr Leu Thr Pro Phe Phe Asp Thr Pro Ile Ala His Cys Val
            115                 120                 125

Ser Met Ala Ser Leu Ile Ser Ala Leu Asp Gln Ile Val Gly Gln Val
        130                 135                 140

Met Lys Gln Phe Pro Gly Thr Val Gly Phe His Ser His Thr Gln Ala
145                 150                 155                 160

Ala Thr Phe Gly Ser Asp Leu Asp Tyr Ala Cys Leu Gly Ser Gly Leu
                165                 170                 175

Glu Met Glu Arg Tyr Gln Phe Cys Glu Gln Pro His Gln Leu Ala
            180                 185                 190

Trp Met Gly Arg Ile Ser Pro Glu Lys Gly Leu Glu Asp Ala Ile Ala
        195                 200                 205

Ala Ala Asp Lys Thr Gly Ile Pro Leu Glu Ile Phe Gly Lys Ile Gln
    210                 215                 220

Asp Asp Gln Tyr Trp Gln Asn Ile Leu Asn Thr Tyr Pro Asn Ala Pro
225                 230                 235                 240

Leu Asn Tyr Arg Gly Phe Leu Asn Thr Asp Glu Leu Gln Gln Gly Leu
                245                 250                 255

Arg Gln Cys Arg Gly Leu Leu Met Thr His Arg Trp Val Glu Ala Phe
            260                 265                 270

Gly Asn Val Ala Ile Glu Ala Leu Ala Cys Gly Val Pro Val Ile Ser
        275                 280                 285

Tyr Arg Arg Gly Gly Pro Ala Glu Ile Val Arg Asp Gly Glu Thr Gly
    290                 295                 300

Trp Leu Val Glu Pro Asp Ser Val Thr Gly Leu Val Asp Ala Ile Ala
305                 310                 315                 320

Lys Phe Glu Gln Ile Asp Arg Arg Gln Cys Arg Ala Val Ala Glu Lys
                325                 330                 335

Glu Tyr Ser Leu Ala Ala Leu Gly Asp Arg Leu Glu Lys Trp Leu Ser
            340                 345                 350

Asp Val Thr Arg Leu Lys Asn
        355
```

<210> SEQ ID NO 3

<211> LENGTH: 359
<212> TYPE: PRT
<213> ORGANISM: Spirulina maxima CY-49

<400> SEQUENCE: 3

```
Met Pro Gln Lys Ser Trp Lys Leu Leu Phe Ile Ser Thr Pro Val Gly
  1               5                  10                  15

Pro Leu Gly Ser Gly Leu Gly Gly Val Glu Leu Thr Leu Leu Asn
             20                  25                  30

Met Ala Lys Ala Leu His Ser Arg Gly His Asp Ile Thr Val Val Ala
             35                  40                  45

Pro Ser Gly Ser Val Leu Glu Ser Leu Ser Val Ile Glu Ile Ser Gly
         50                  55                  60

Lys Leu Gln Pro Ile Ala Gln Asn Gln Asp Arg Asp Ser Leu Ile Thr
 65                  70                  75                  80

Ile Pro Glu Asn Ser Val Leu Gly Asn Met Trp Glu Tyr Gly Arg Gln
                 85                  90                  95

Val Gln Thr Asn Tyr His Ala Ile Val Asn Phe Ala Phe Asp Trp Leu
            100                 105                 110

Pro Phe Tyr Leu Thr Pro Phe Pro Thr Pro Ile Ala His Trp Val
        115                 120                 125

Ser Met Gly Ser Leu Ile Ser Ala Leu Asp Gln Ile Val Val Glu Val
    130                 135                 140

Met Lys Gln Phe Pro Gly Thr Val Gly Phe Tyr Ser His Thr Gln Ala
145                 150                 155                 160

Ala Thr Phe Gly Ser Asp Leu Gly Tyr Ala Cys Leu Gly Ser Gly Leu
                165                 170                 175

Glu Met Asp Arg Tyr Gln Phe Cys Asp Gln Pro His Gln Gln Leu Ala
            180                 185                 190

Trp Met Gly Arg Ile Ser Pro Glu Lys Gly Leu Glu Asp Ala Ile Ala
        195                 200                 205

Ala Ala Asp Lys Thr Gly Ile Pro Leu Ala Ile Phe Gly Lys Ile Gln
    210                 215                 220

Asp Glu Gln Tyr Trp Gln Asn Ile Leu Asn Thr Tyr Pro Asn Ala Pro
225                 230                 235                 240

Leu Asn Tyr Arg Gly Phe Leu Asn Thr Asp Glu Leu Gln Gln Gly Leu
                245                 250                 255

Arg Glu Cys Arg Gly Leu Leu Met Thr His Arg Trp Val Glu Ala Phe
            260                 265                 270

Gly Asn Val Ala Ile Glu Ala Leu Ala Cys Gly Val Pro Val Ile Ser
        275                 280                 285

Tyr Arg Arg Gly Gly Pro Ala Glu Ile Val Arg Asp Gly Glu Thr Gly
    290                 295                 300

Trp Leu Val Glu Pro Asp Ser Val Thr Gly Leu Val Asp Ala Ile Ala
305                 310                 315                 320

Lys Leu Glu Gln Ile Asp Arg Arg Gln Cys Arg Ala Leu Ala Glu Lys
                325                 330                 335

Glu Tyr Ser Leu Val Ala Leu Gly Asp Arg Leu Glu Thr Trp Leu Ser
            340                 345                 350

Asp Val Ile Ala Leu Lys Asn
        355
```

<210> SEQ ID NO 4
<211> LENGTH: 356
<212> TYPE: PRT
<213> ORGANISM: Unknown

<220> FEATURE:
<223> OTHER INFORMATION: Unidentified cyanobacteria sp.

<400> SEQUENCE: 4

Leu Ser Arg Lys Leu Leu Phe Leu Ser Thr Pro Val Gly Phe Leu Gly
1               5                   10                  15

Ser Gly Gly Gly Gly Val Glu Leu Thr Ile Tyr Asn Leu Ala Arg
            20                  25                  30

Thr Leu Asn Lys Gln Gly Tyr Ala Val Arg Val Ala Pro Glu Ala
        35                  40                  45

Ser Gln Leu Gln Asp Ile Pro Leu Ile Thr Ile Ala Gly Asn Ala Gln
    50                  55                  60

Ile Ser Ala Gln Ser Gln Asp Arg Glu Ala Pro Ile Leu Ile Pro Glu
65                  70                  75                  80

Asn Ala Val Leu Ala Asn Met Trp His Tyr Ala Gln Gln Val Gln Asn
                85                  90                  95

Glu Tyr Asp Leu Ile Val Asn Phe Ala Tyr Asp Trp Leu Pro Phe Tyr
            100                 105                 110

Leu Thr Pro Phe Phe Ala Thr Pro Val Ala His Leu Val Ser Met Ala
        115                 120                 125

Ser Val Ser Leu Ala Met Asp Asn Ile Ile Gln Lys Thr Tyr Arg Ser
    130                 135                 140

Phe Pro His Ser Leu Ala Phe His Thr Val Thr Gln Ala Glu Thr Phe
145                 150                 155                 160

Ser Leu Ser Pro Pro Tyr Arg Arg Leu Ala Asn Gly Leu Asp Val Ser
                165                 170                 175

Leu Tyr Gln Phe Arg Ala Asp Pro Ser Pro Cys Leu Ala Trp Val Gly
            180                 185                 190

Arg Ile Ala Pro Glu Lys Ala Leu Glu Gly Ala Ile Ala Ala Cys Gln
        195                 200                 205

Gln Leu Gly Val Pro Leu Arg Val Phe Gly His Ile Ser Asn Pro Leu
    210                 215                 220

Tyr Trp Gln Asn Leu Gln Asp Thr Tyr Ser Phe Asp Leu Val Asp Tyr
225                 230                 235                 240

Arg Gly Phe Leu Pro Thr Gly Ser Leu Gln Lys Glu Leu Gly Asp Cys
                245                 250                 255

Phe Gly Leu Leu Met Thr Pro Gly Trp Val Glu Ala Phe Gly Asn Val
            260                 265                 270

Ala Ile Glu Ala Leu Ala Cys Gly Val Pro Val Val Ala Tyr Arg Arg
        275                 280                 285

Gly Gly Pro Val Glu Ile Ile Glu Glu Gly Lys Thr Gly Phe Leu Val
    290                 295                 300

Glu Pro Asp Ser Ile Glu Gly Leu Val Thr Gly Ile Lys Asn Leu Asp
305                 310                 315                 320

Arg Ile Asp Arg Tyr Ser Cys Arg Ala Val Val Glu Gln Lys Tyr Ser
                325                 330                 335

Leu Glu Ala Leu Ala Asn Arg Ala Ile Asn Trp Phe Asp Glu Ile Phe
            340                 345                 350

Ala Arg Lys Lys
        355

<210> SEQ ID NO 5
<211> LENGTH: 356
<212> TYPE: PRT
<213> ORGANISM: Unknown
<220> FEATURE:

<223> OTHER INFORMATION: Unidentified cyanobacteria sp.

<400> SEQUENCE: 5

```
Leu Ser Arg Lys Leu Leu Phe Leu Ser Thr Pro Val Gly Phe Leu Gly
  1               5                  10                  15

Ser Gly Asp Gly Gly Val Glu Leu Thr Ile Tyr Asn Leu Ala Arg
             20                  25                  30

Thr Leu Asn Lys Gln Gly Tyr Ala Val Arg Val Ala Ala Pro Glu Ala
         35                  40                  45

Ser Gln Leu Gln Asp Ile Pro Leu Ile Thr Met Ala Gly Asn Ala Gln
     50                  55                  60

Ile Ser Ala Gln Ser Gln Gly Arg Glu Ala Pro Ile Leu Met Pro Glu
 65                  70                  75                  80

Asn Ala Val Leu Ala Asn Met Trp His Tyr Ala Gln Gln Val Gln Lys
                 85                  90                  95

Gln Tyr Asp Leu Ile Val Asn Phe Ala Tyr Asp Trp Leu Pro Phe Tyr
            100                 105                 110

Leu Thr Pro Phe Phe Ala Thr Pro Val Ala His Leu Val Ser Met Ala
        115                 120                 125

Ser Val Ser Leu Ala Met Asp His Ile Asn Glu Lys Thr Tyr Ser Asn
    130                 135                 140

Phe Pro His Leu Leu Ala Phe His Thr Leu Ala Gln Ala Glu Thr Phe
145                 150                 155                 160

Ser Leu Ser Pro Pro Tyr Arg Cys Leu Ala Asn Gly Leu Asp Val Ser
                165                 170                 175

Leu Tyr Gln Phe Arg Asp Asp Pro Ser Pro Cys Leu Ala Trp Val Gly
            180                 185                 190

Arg Ile Ala Pro Glu Lys Ala Leu Glu Asp Ala Ile Ala Ala Cys Gln
        195                 200                 205

Gln Leu Gly Val Pro Leu Arg Val Phe Gly His Ile Ser Asp Pro Leu
    210                 215                 220

Tyr Trp Gln Asn Ser Gln Asp Thr Tyr Ser Phe Asp Leu Val Asp Tyr
225                 230                 235                 240

Arg Gly Phe Leu Pro Thr Gly Ser Leu Gln Lys Glu Leu Gly Asp Cys
                245                 250                 255

Phe Gly Leu Leu Met Thr Pro Arg Trp Val Glu Ala Phe Gly Asn Val
            260                 265                 270

Ala Ile Glu Ala Leu Ala Cys Gly Val Pro Val Val Ala Tyr Arg Arg
        275                 280                 285

Gly Gly Pro Val Glu Ile Ile Glu Glu Gly Lys Thr Gly Phe Leu Val
    290                 295                 300

Glu Pro Asp Ser Ile Glu Gly Leu Val Thr Gly Ile Lys Asn Leu Asp
305                 310                 315                 320

Arg Ile Asp Arg Tyr Ser Cys Arg Ala Val Val Glu Gln Lys Tyr Ser
                325                 330                 335

Leu Glu Ala Ser Ala Asn Arg Ala Ile Asn Trp Phe Glu Glu Ile Phe
            340                 345                 350

Ala Arg Lys Lys
        355
```

<210> SEQ ID NO 6
<211> LENGTH: 1080
<212> TYPE: DNA
<213> ORGANISM: Synechococcus PCC7942

<400> SEQUENCE: 6

```
atgactgccc accgttttct gtttgtatca acacccgtcg gcccttgggg gtcggggcga    60
ggggcggtg ttgaactgac cctgcccaat ttagccaagg ctctgaccca gcgagggcac   120
caagtcagcg tgctcgcgcc ggctggatcg gtgctgcccg atttgccgct ggaaacggtg   180
cctgggactt ggcaaagcac ggctcaaagt cacgggcgcg ccactcctgc tgagattcct   240
gctgagagtg ttttagcccg gctctgggat cgagctcacc agcagcaagc cgactttgac   300
ctgatcctca acttcgccta cgactggcta ccgctatatc tgacgccgtt tttcaagacg   360
cctgtcgccc atttgatcag catgggatcc ctatctgagg tgatggatca ggcgatcgcc   420
acaagcctcg atcgctatcc cggcagcatc gctgtccaca gtctggctca ggcagcaacc   480
tttcccttttg gcgatcgctg cctttgtatc ggcaatgccc ttgacctagc agcctatggg   540
tttaacccag agccagagcc ggtcttgggc tgggtaggac ggattgcacc agaaaagggc   600
ctagaagatg ccattcaagc cgctcaacag gctggcctcc cgttgcgggt ctggggtgcc   660
ctgactgaac ccgactattg gcaacgactc aacagcagtt tggcgatcg gccgtcagc   720
tatcagggct tcgtcagtac cgatgagttg caacgtggct tgggccgctg ccaaggcctg   780
ttaatgaccc caaaatgggt agaagccttt ggcaacgtcg ccattgaagc cctcgcctgt   840
gggctaccag tgatagccta tgcccgcggc ggacccttgg aaattattga gcagggcaag   900
agtggctggc tggtagaacc cgatcaacag gctgctctcg tcaacgcaat gggcaactg   960
tctagcctcg atcgcgctta ctgtcgagcc caagccgaag cacggttttc cttggctgcg   1020
atgggtcaac gtctagaagc gtggctactc cccctcttgt cccgagcccg aggcttctag   1080
```

<210> SEQ ID NO 7
<211> LENGTH: 1080
<212> TYPE: DNA
<213> ORGANISM: Spirulina platensis CY-7

<400> SEQUENCE: 7

```
atgactccaa caagctggaa attactattt atatcaaccc ccgtaggtcc cctaggttca    60
ggattaggtg ggggagtcga attaacatta ttgaatatgg caaaagccctt aaaaagccga   120
ggtcatgata taaccgttgt tgcgccttct gggtcagtgt tagagtccct atcaattata   180
gaaattccgg gggaactaca accgatcgcc caaaatcaag accgagattc tctgattacc   240
atacccgaaa attctgtgtt aggaaatatg tgggaatatg ggcgacaggt acagacaaac   300
tatcatgcaa ttgtcaattt tgcctttgat tggttaccat tttatctcac ccccttttttc   360
gatactccca tcgctcattg cgtcagtatg gcttccctaa tttccgcctt agatcagata   420
gttggtcagg tgatgaaaca gtttccgggg actgtcggat tcatagcca tacccaagcc   480
gccacctttg gttcagacct agactatgct tgtttaggaa gtggcttaga aatggagcgc   540
tatcagttttt gtgagcaacc ccatcaacaa ctagcttgga tggggcgtat ttccccggaa   600
aaaggcttag aggatgcgat cgcggcggcg gataaaacag gtatccctct ggaaattttt   660
ggcaaaattc aggatgatca atattggcaa aatatcctga atacttatcc gaatgcaccc   720
ttaaattacc gggggatttttt gaatacagat gaactacaac agggtctgcg tcaatgtcgg   780
ggttttattaa tgactcatcg ctgggtagaa gcctttggaa atgtcgctat tgaagcctta   840
gcctgtgggg ttcccgtgat tagttatcga cggggaggac ccgccgaaat tgtccgagat   900
ggtgaaacgg gttggctagt tgaacccgac agcgtaacgg gtttggtcga tgcgatcgcc   960
aaattcgagc aaattgaccg ccgccaatgt cgcgctgta ccgaaaagga atattcctta  1020
gcagctttag gcgatcgctt agaaaaatgg ttatctgatg ttacccggct taaaaattga  1080
```

<210> SEQ ID NO 8
<211> LENGTH: 1080
<212> TYPE: DNA
<213> ORGANISM: Spirulina maxima CY-49

<400> SEQUENCE: 8

```
atgcctcaaa aaagctggaa attactattt atatccaccc cggtcggtcc cctgggttca      60
ggattagggg ggggagtcga attaacattg ttgaatatgg caaaagcctt acacagccga     120
ggtcatgata taaccgttgt tgcgccttct gggtcagtgt tagagtccct atcagttata     180
gaaatttcgg ggaaactaca accgatcgcc caaaatcaag accgagattc tctgattacc     240
ataccggaaa attctgtgtt aggaaatatg tgggaatatg gcgacaggt acagacaaac      300
tatcatgcaa ttgtcaattt tgcctttgat tggctaccat tttatctgac tccttttttc     360
ccgactccga tcgctcactg ggtgagtatg ggttccctaa tttccgcctt agatcagata     420
gttgttgagg tgatgaaaca gtttccgggg actgtcggat tttatagcca tacccaagcc     480
gccacctttg gttcagacct aggctatgct tgtttaggaa gtggcttaga aatggatcgc     540
tatcagtttt gtgatcaacc ccatcaacaa ctagcttgga tgggtcgtat ttccccggaa     600
aaaggcttag aggatgcgat cgcggcggcg gataaaacag gtatccctct ggcaattttt     660
ggcaaaattc aggatgagca atattggcaa atatcctga atacttatcc gaatgcgccc      720
ctaaattatc ggggattttt gaatacagat gaactacaac agggtctgcg tgaatgtcga     780
ggtttattaa tgactcatcg ctgggtagaa gcctttggaa atgtcgctat tgaagcctta     840
gcctgtgggg ttccggtgat tagttatcga cggggtggac ccgccgaaat tgtccgagat     900
ggtgaaacgg gttggctagt cgaacccgac agcgtaacgg gttggtcga tcgatcgcc      960
aaattagagc aaattgaccg ccgccaatgt cgcgctttag ccgaaaagga atattcctta    1020
gtagctttag gcgatcgctt agaaacatgg ttatccgatg tgatcgcgct taaaaattga    1080
```

<210> SEQ ID NO 9
<211> LENGTH: 1071
<212> TYPE: DNA
<213> ORGANISM: Unknown
<220> FEATURE:
<223> OTHER INFORMATION: Unidentified cyanobacteria sp.

<400> SEQUENCE: 9

```
ttgagtcgaa aactgttgtt tctctcgacc cccgtgggat ttttgggatc gggggggcggc     60
ggtggcgtag aattaaccat ttataatctc gcgcgcactc tgaataagca agggtatgcg    120
gtgcgggtag tggctccaga agcctcgcaa ttgcaggata tccccttgat cactatagcg    180
ggaaatgccc agatttccgc ccagagtcaa gaccgggaag ccccgatttt aatacccgaa    240
aatgccgttt tggccaatat gtggcactac gcccaacagg tacaaaatga gtacgattta    300
attgttaatt ttgcctacga ttggctccct tttatctca ctccttttt tgctactccc      360
gtcgcccatt tagtcagcat ggcttccgtt tcttggcga tggataatat tattcaaaaa     420
acttaccgca gttttcccca ttcactcgct tttcacaccg tcacccaagc agaaactttc    480
tccctctctc ccccctatcg ccgtttggct aatggtttgg acgtatcttt gtatcagttt    540
cgggctgatc cctcccctg tctagcctgg gtgggacgga tcgcgccaga aaaagcttta    600
gaaggtgcga tcgctgcttg tcaacagtta ggtgtcccct tacgggtttt cggtcatatt    660
tccaatcctc tctactggca aaatttacag gataccta gtttcgattt agtcgattat      720
cgcgggtttt tgcccactgg gagcctacaa aaagagctag gcgactgttt tggcctgttg    780
```

```
atgaccccgg gctgggttga ggcttttggt aacgtggcta ttgaagcttt agcctgtggt    840
gttcccgtag ttgcctatcg tcgcggtggt ccggtagaaa ttattgaaga gggaaaaact    900
ggttttttag ttgaacccga tagtatcgag ggattagtta caggaattaa aaatttagac    960
cggatcgatc gatattcttg tcgtgcagta gtcgagcaaa atattccct  agaagctttg   1020 gcaaatcgag ctattaattg gtttgatgaa attttttgctc gcaaaaaata a           1071
```

<210> SEQ ID NO 10
<211> LENGTH: 1071
<212> TYPE: DNA
<213> ORGANISM: Unknown
<220> FEATURE:
<223> OTHER INFORMATION: Unidentified cyanobacteria sp.

<400> SEQUENCE: 10

```
ttgagtcgaa aactgttatt tctctccacc cccgtgggat ttttgggatc gggggacggc     60
ggtggcgtag aattaactat ttataatctc gctcgcactc tgaataagca agggtatgcg    120
gtgcgggtag cggctccaga agcctcgcaa ttgcaggata tccccttgat cactatggca    180
ggaaatgccc agatttccgc ccaaagtcaa ggccgggaag ccccgatttt aatgccagaa    240
aatgccgttt tggccaatat gtggcactac gcccaacaag tacaaaaaca gtacgatttg    300
attgtcaatt ttgcctacga ttggctccct ttttacctca ctcctttttt tgccactccc    360
gtcgcccatt tagtcagcat ggcttccgtt tctttggcga tggatcatat taatgaaaaa    420
acctacagca attttcccca tttactcgct tttcacaccc ttgcccaagc agaaactttc    480
tccctctctc cccctatcg  ctgtttggct aatggtttag acgtatcttt gtatcagttt    540
cgggacgatc cttccccctg tctagcctgg gtgggacgga ttgccccgga aaaggctttg    600
gaagatgcga tcgcagcttg tcaacagtta ggtgtcccctt tacgggtttt cggtcatatt    660
tccgatcctc tctactggca aaattcacag gataacctata gtttcgattt agtcgattat    720
cgcgggtttt tgcccaccgg gagcctacaa aaagagttag gcgactgttt tggcctgttg    780 atgacccgc gctgggttga ggcttttggt aacgtggcta ttgaagcttt agcctgtggt    840
gttcccgtag ttgcctatcg tcgcggtggt ccggtagaaa ttattgaaga gggaaaaact    900
ggttttttag ttgaacccga tagtatcgag ggattagtta caggaattaa aaatttagac    960
cggatcgatc gatattcttg tcgtgcagta gtcgagcaaa atattccct  agaagcttcg   1020 gcaaatcgag ctattaattg gtttgaagaa attttttgctc gcaaaaaata a           1071
```

<210> SEQ ID NO 11
<211> LENGTH: 22
<212> TYPE: DNA
<213> ORGANISM: Artificial Sequence
<220> FEATURE:
<223> OTHER INFORMATION: Primer

<400> SEQUENCE: 11

```
gttcaggawt aggaggtgga gt                                               22
```

<210> SEQ ID NO 12
<211> LENGTH: 22
<212> TYPE: DNA
<213> ORGANISM: Artificial Sequence
<220> FEATURE:
<223> OTHER INFORMATION: Primer

<400> SEQUENCE: 12

```
cgcytcaatw gctacatttc ca                                               22
```

```
<210> SEQ ID NO 13
<211> LENGTH: 24
<212> TYPE: DNA
<213> ORGANISM: Artificial Sequence
<220> FEATURE:
<223> OTHER INFORMATION: Primer

<400> SEQUENCE: 13
acgactggct mycgytttay ctga                                              24

<210> SEQ ID NO 14
<211> LENGTH: 22
<212> TYPE: DNA
<213> ORGANISM: Artificial Sequence
<220> FEATURE:
<223> OTHER INFORMATION: Primer

<400> SEQUENCE: 14
gcytccaccc ayttrggggt ca                                                22

<210> SEQ ID NO 15
<211> LENGTH: 30
<212> TYPE: DNA
<213> ORGANISM: Artificial Sequence
<220> FEATURE:
<223> OTHER INFORMATION: Primer

<400> SEQUENCE: 15
accggggatt tttgaataca gatgaactac                                        30

<210> SEQ ID NO 16
<211> LENGTH: 29
<212> TYPE: DNA
<213> ORGANISM: Artificial Sequence
<220> FEATURE:
<223> OTHER INFORMATION: Primer

<400> SEQUENCE: 16
gatagggact ctaacactga cccagaagg                                         29

<210> SEQ ID NO 17
<211> LENGTH: 25
<212> TYPE: DNA
<213> ORGANISM: Artificial Sequence
<220> FEATURE:
<223> OTHER INFORMATION: Primer

<400> SEQUENCE: 17
gatgaactac aacagggtct gcgtc                                             25

<210> SEQ ID NO 18
<211> LENGTH: 27
<212> TYPE: DNA
<213> ORGANISM: Artificial Sequence
<220> FEATURE:
<223> OTHER INFORMATION: Primer

<400> SEQUENCE: 18
cggcttttta aggcttttgc catattc                                           27

<210> SEQ ID NO 19
<211> LENGTH: 18
<212> TYPE: DNA
<213> ORGANISM: Artificial Sequence
<220> FEATURE:
<223> OTHER INFORMATION: Primer
```

```
<400> SEQUENCE: 19
acagggtctg cgtgaatg                                            18

<210> SEQ ID NO 20
<211> LENGTH: 21
<212> TYPE: DNA
<213> ORGANISM: Artificial Sequence
<220> FEATURE:
<223> OTHER INFORMATION: Primer

<400> SEQUENCE: 20
ctctaacact gacccagaag g                                        21

<210> SEQ ID NO 21
<211> LENGTH: 19
<212> TYPE: DNA
<213> ORGANISM: Artificial Sequence
<220> FEATURE:
<223> OTHER INFORMATION: Primer

<400> SEQUENCE: 21
gtctgcgtga atgtcgagg                                           19

<210> SEQ ID NO 22
<211> LENGTH: 19
<212> TYPE: DNA
<213> ORGANISM: Artificial Sequence
<220> FEATURE:
<223> OTHER INFORMATION: Primer

<400> SEQUENCE: 22
atgacctcgg ctgtgtaag                                           19

<210> SEQ ID NO 23
<211> LENGTH: 24
<212> TYPE: DNA
<213> ORGANISM: Artificial Sequence
<220> FEATURE:
<223> OTHER INFORMATION: Primer

<400> SEQUENCE: 23
cgggagccta caaaaagagc tagg                                     24

<210> SEQ ID NO 24
<211> LENGTH: 26
<212> TYPE: DNA
<213> ORGANISM: Artificial Sequence
<220> FEATURE:
<223> OTHER INFORMATION: Primer

<400> SEQUENCE: 24
aatatgatcc atcgccaaag aaacgg                                   26

<210> SEQ ID NO 25
<211> LENGTH: 29
<212> TYPE: DNA
<213> ORGANISM: Artificial Sequence
<220> FEATURE:
<223> OTHER INFORMATION: Primer

<400> SEQUENCE: 25
cctacaaaaa gagctaggcg actgttttg                                29

<210> SEQ ID NO 26
<211> LENGTH: 23
```

```
<212> TYPE: DNA
<213> ORGANISM: Artificial Sequence
<220> FEATURE:
<223> OTHER INFORMATION: Primer

<400> SEQUENCE: 26
ccaaagaaac ggaagccatg ctg                                             23

<210> SEQ ID NO 27
<211> LENGTH: 38
<212> TYPE: DNA
<213> ORGANISM: Artificial Sequence
<220> FEATURE:
<223> OTHER INFORMATION: Primer

<400> SEQUENCE: 27
catatgactc caacaagctg gaaattacta tttatatc                             38

<210> SEQ ID NO 28
<211> LENGTH: 34
<212> TYPE: DNA
<213> ORGANISM: Artificial Sequence
<220> FEATURE:
<223> OTHER INFORMATION: Primer

<400> SEQUENCE: 28
ggatcctcaa tttttaagcc gggtaacatc agat                                 34

<210> SEQ ID NO 29
<211> LENGTH: 32
<212> TYPE: DNA
<213> ORGANISM: Artificial Sequence
<220> FEATURE:
<223> OTHER INFORMATION: Primer

<400> SEQUENCE: 29
catatgcctc aaaaaagctg gaaattacta tt                                   32

<210> SEQ ID NO 30
<211> LENGTH: 31
<212> TYPE: DNA
<213> ORGANISM: Artificial Sequence
<220> FEATURE:
<223> OTHER INFORMATION: Primer

<400> SEQUENCE: 30
gaattcttca atttttaagc gcgatcacat c                                    31

<210> SEQ ID NO 31
<211> LENGTH: 33
<212> TYPE: DNA
<213> ORGANISM: Artificial Sequence
<220> FEATURE:
<223> OTHER INFORMATION: Primer

<400> SEQUENCE: 31
catatgagtc gaaaactgtt atttctctcc acc                                  33

<210> SEQ ID NO 32
<211> LENGTH: 35
<212> TYPE: DNA
```

```
<213> ORGANISM: Artificial Sequence
<220> FEATURE:
<223> OTHER INFORMATION: Primer

<400> SEQUENCE: 32
ggatccttat tttttgcgag caaaaatttc ttcaa                                35
```

PROTEINS WITH PTERIDINE GLYCOSYLTRANSFERASE ACTIVITY AND ANALYSIS METHOD USING THE SAME

This is a National Phase Application filed under 35 U.S.C. §371 as a national stage of PCT/KR2009/001591, filed on Mar. 30, 2009, claiming the benefit of Korean Patent Application 10-2008-0030804, filed on Apr. 2, 2008, and claiming the benefit of Korean Patent Application 10-2009-0016695, filed on Feb. 27, 2009, the content of each of which is hereby incorporated by reference in its entirety.

TECHNICAL FIELD

The present invention relates to a protein having pteridine glycosyltransferase activity and an analytical method using the same. The analytical method includes a simultaneous quantitative analysis of both tetrahydrobiopterin and its oxidized forms and a selective quantitative analysis of tetrahydrobiopterin.

The Sequence Listing submitted in text format (.txt) on Nov. 17, 2010, named "10012010 sequence listing Corrected.txt", (created on Monday, Nov. 15, 2010, 26.4 KB), is incorporated herein by reference.

BACKGROUND ART

Tetrahydrobiopterin, a cofactor for aromatic amino acid hydroxylases, is associated with various diseases (Kaufman S & Fisher D B. (1974) Pterin-requiring aromatic amino acid hydroxylases. In: Hayaishi O, ed. Molecular Mechanisms of Oxygen Activation. New York: Academic Press pp 285-369).

Atypical phenylketonuria (PKU) is one of the representative diseases originated from tetrahydrobiopterin deficiency. An infant born having genetic deficiency in tetrahydrobiopterin biosynthesis or regeneration (that is an infant with PKU) shows dysfunction of phenylalanine hydroxylase, thereby increasing phenylalanine concentration in the blood (Nichol C A, Smith G K, Duch D S. (1985) Biosynthesis and metabolism of tetrahydrobiopterin and molybdopterin. Annu Rev Biochem. 54:729764; Duch D S, Smith G K (1991) Biosynthesis and function of tetrahydrobiopterin. J. Nutr. Biochem., 2: 411-423). The patients suffering from PKU also show dysfunction in tyrosine and tryptophan hydroxylase activities, which results in insufficient biosynthesis of neurotransmitters such as dopamine and serotonin in the brain.

In addition, it has been reported that tetrahydrobiopterin deficiency causes dopa-responsive dystonia, which is one of the genetic neuronal diseases (Ichinose H, Ohye T, Takahashi E, et al. (1994) Hereditary progressive dystonia with marked diurnal fluctuation caused by mutation in the GTP cyclohydrolase I gene. Nat Genet 8:236-241). It has been also reported that tetrahydrobiopterin deficiency is associated with Parkinson's disease. And also, it has been reported that patients with Alzheimer's disease, depression, autism, or schizophrenia shows lower concentration of tetrahydrobiopterin in body fluids than normal people (Thony, B., Auerbach, G. and Blau, N. (2000) Tetrahydrobiopterin biosynthesis, regeneration and functions. Biochem. J. 347, 116; H. Tiemeier, D. Fekkes, A. Hofman, H. R. van Tuijl, A. J. Kiliaan, M. M. Breteler (2006) Plasma pterins and folate in late life depression: The Rotterdam study. Psychiatry Res. 145: 199-206; M. A. Richardson, L. L. Read, M. A. Reilly, J. D. Clelland, C. L. Clelland (2007) Analysis of plasma biopterin levels in psychiatric disorders suggests a common BH4 deficit in schizophrenia and schizoaffective disorder, Neurochem Res. 32: 107-113; T. Danfors, A. L. von Knorring, P, Hartvig, B. Langstrom, R. Moulder, B. Stromberg, R. Torstenson, U. Wester, Y. Watanabe, O. Eeg-Olofsson (2005) Tetrahydrobiopterin in the treatment of children with autistic disorder: a double-blind placebo-controlled crossover study, J. Clin. Psychopharmacol. 25: 485-489). Furthermore, vitiligo, which shows melanin deficiency in epidermis, is originated from dysfunction of tetrahydrobiopterin biosynthesis (Schallreuter K U, Zschiesche M & Moore J et al. (1998) In vivo evidence for compromised phenylalanine metabolism in vitiligo. Biochem Biophys Res Commun 243: 395-399).

Tetrahydrobiopterin also plays a critical role in endothelial dysfunctions such as diabetes, hypertension, myocardial infraction, and stroke, as a cofactor and regulator of nitric oxide synthase (NOS) (Schmidt T S, Alp N J (2007) Mechanisms for the role of tetrahydrobiopterin in endothelial function and vascular disease. Clinical Science 113: 47-63; and Moens A L, Kass D A (2006) Tetrahydrobiopterin and cardiovascular disease. Arterioscler Thromb Vasc Biol 26: 2439-2444).

In order to diagnose said various diseases such as atypical phenylketonuria, dystonia, Parkinson's disease, Alzheimer's disease, depression, autism, schizophrenia, vitiligo, and endothelial dysfunctions, it is required to effectively analyze tetrahydrobiopterin in a sample obtained from patients, e.g., blood (plasma and/or serum), cerebrospinal fluid, urine, and other tissues.

Meanwhile, tetrahydrobiopterin is functional in the fully reduced form (i.e., tetrahydro form). However, it is converted into non-functional oxidized forms, i.e., dihydrobiopterin and biopterin, under oxidative stress conditions, such as hypertension or diabetes. Therefore, both tetrahydrobiopterin and its oxidized forms (i.e., dihydrobiopterin and biopterin) may simultaneously exist in the body. Especially, in cardiovascular diseases which are known that the major cause thereof is oxidative stress, the oxidation of tetrahydrobiopterin is one of the serious problems. Recently, the ratio of tetrahydrobiopterin/(dihydrobiopterin+biopterin) or the ratio of tetrahydrobiopterin/(tetrahydrobiopterin+dihydrobiopterin+biopterin) is used as a key index in cardiovascular diseases (Yada T, Kaji S, Akasaka T, et al. (2007) Changes of asymmetric dimethylarginine, nitric oxide, tetrahydrobiopterin, and oxidative stress in patients with acute myocardial infarction by medical treatments. Clinical Hemorheology and Microcirculation 37: 269-276; and Taylor N E, Maier K G, Roman R J, Cowley A W (2006) NO synthase uncoupling in the kidney of Dahl rats: Role of dihydrobiopterin. Hypertension. 48: 1066-1071). Therefore, it is important to quantitatively analyze each amount of tetrahydrobiopterin and its oxidized forms in a biological sample.

Conventional analytical methods for tetrahydrobiopterin in a biological sample are based on fluorescence-characteristics of its oxidized forms. That is, tetrahydrobiopterin is oxidized with an acidic iodine solution and then quantitative analysis is performed using fluorometric high performance liquid chromatography (fluorometric HPLC). However, according to the conventional analytical methods, dihydrobiopterin and biopterin, in addition to tetrahydrobiopterin, are also oxidized and detected at the same position on HPLC. Therefore, the conventional analytical methods have a drawback that each tetrahydrobiopterin and its oxidized forms cannot be analyzed separately.

In order to solve the problem, Fukushima T et al. have developed an analytical method using alkaline iodine oxidation (Fukushima T, Nixon J C (1980) Analysis of reduced forms of biopterin in biological tissues and fluids. Anal Biochem 102: 176-88). Under the condition of alkaline iodine oxidation, tetrahydrobiopterin is oxidized to pterin with cleavage of the side chain thereof; and dihydrobiopterin is oxidized to biopterin. However, the analytical method using alkaline iodine oxidation requires preparing a separate sample, in addition to a sample for acidic iodine oxidation, and also performing the HPLC analyses two times.

As another method, there has been reported a method, which includes performing HPLC in anaerobic conditions to separate tetrahydrobiopterin from its oxidized forms and then analyzing them with electrochemical detector (ECD) (Lunte C E, Kissinger P T (1983) The determination of pterins in biological samples by liquid chromatography/electrochemistry. Anal. Biochem 129: 377-386). However, the quantitative analysis using ECD shows significant deviations in each sample. In order to this problem, there has been also reported an improved method, wherein the samples eluted through the HPLC are oxidized with acidic iodine solution and then measured with a fluorometric detector (Hyland K (1985) Estimation of tetrahydro, dihydro and fully oxidized pterins by high performance liquid chromatography using sequential electrochemical and fluorometric detection. J Chromatogr. 343(1): 3541). However, this method requires additional equipment for sample treatment.

Because of the above problems, it is difficult to quantitatively analyze tetrahydrobiopterin and its oxidized forms separately. And also, according to the literatures, significant deviations are shown in amount of tetrahydrobiopterin obtained from the same biological sample. Therefore, there is a need to develop a simple, prompt, and accurate method for quantitative analysis of each tetrahydrobiopterin and its oxidized forms in a sample, including biological samples.

DISCLOSURE

Technical Problem

It was found in the present invention that specific proteins isolated from microorganism convert all of the tetrahydrobiopterin in a sample to its glycosylated product exclusively (i.e., without competitive reaction), even though the sample has also dihydrobiopterin and biopterin; and therefore that, using the proteins, it is possible to quantitatively analyze tetrahydrobiopterin and its oxidized forms, separately. And also, it was found that very low level of tetrahydrobiopterin in a sample can be analyzed using the proteins; and that, through single HPLC analysis, it is possible to perform a simultaneous quantitative analysis of both tetrahydrobiopterin and its oxidized forms or to perform a selective quantitative analysis of tetrahydrobiopterin.

Therefore, the present invention provides a method for simultaneous quantitative analysis of both tetrahydrobiopterin and its oxidized forms in a sample.

And also, the present invention provides a method for selective quantitative analysis of tetrahydrobiopterin in a sample.

And also, the present invention provides a protein having pteridine glycosyltransferase activity.

And also, the present invention provides a polynucleotide encoding the protein having pteridine glycosyltransferase activity, a vector comprising the polynucleotide, and a transformant obtained by transforming a host cell with the vector.

Technical Solution

In accordance with an aspect of the present invention, there is provided a method for simultaneous quantitative analysis of both tetrahydrobiopterin and its oxidized forms (i.e., dihydrobiopterin and biopterin) in a sample, which comprises:

(a) adding a sample to an enzyme solution comprising a protein selected from the group consisting of proteins as set forth in SEQ ID NOs: 1 to 5 and UDP-glucose or UDP-xylose and then performing an enzymatic reaction;

(b) oxidizing the reaction mixture obtained in Step (a) and then measuring each amount of biopterin and biopterin-glycoside product; and (c) obtaining an amount of tetrahydrobiopterin from the amount of biopterin-glycoside product obtained from Step (b), using a calibration curve between biopterin and biopterin-glycoside product.

In accordance with another aspect of the present invention, there is provided a method for selective quantitative analysis of tetrahydrobiopterin in a sample, which comprises:

(a') adding a sample to an enzyme solution comprising a protein selected from the group consisting of proteins as set forth in SEQ ID NOs: 1 to 5 and UDP-glucose or UDP-xylose and then performing an enzymatic reaction; and (b') measuring an amount of a glycosylated product of tetrahydrobiopterin in the reaction mixture obtained in Step (a').

In accordance with still another aspect of the present invention, there is provided a protein having pteridine glycosyltransferase activity, selected from the group consisting of proteins as set forth in SEQ ID NOs: 2 to 5.

In accordance with still another aspect of the present invention, there is provided a polynucleotide encoding a protein having pteridine glycosyltransferase activity, selected from the group consisting of proteins as set forth in SEQ ID NOs: 2 to 5, preferably the polynucleotide selected from the group consisting of polynucleotides as set forth in SEQ ID NOs: 7 to 10.

In accordance with still another aspect of the present invention, there is provided a vector comprising a polynucleotide and a transformant obtained by transforming a host cell with the vector.

Advantageous Effects

The analytical method according to the present invention is a bioassay method using a protein selected from the group consisting of proteins as set forth in SEQ ID NOs: 1 to 5. In accordance with the analytical method, it is possible to perform a simultaneous quantitative analysis of both tetrahydrobiopterin and its oxidized forms or to perform a selective quantitative analysis of tetrahydrobiopterin. The analytical method according to the present invention is based on the facts that all of the tetrahydrobiopterin in a sample are converted to its glycosylated product without competitive reaction, even though the sample also contains dihydrobiopterin and biopterin; and that there is 1:1 ratio of quantitative relationship in amounts of between tetrahydrobiopterin and its glycosylated form. Especially, in accordance with the analytical method of the present invention, very low level of tetrahydrobiopterin in a sample (e.g., not more than 1 μM) can be effectively analyzed. And also, through single HPLC analysis, it is possible to perform a simultaneous quantitative analysis of both tetrahydrobiopterin and its oxidized forms or to perform a selective quantitative analysis of tetrahydrobiopterin. Therefore, the analytical method of the present invention may be usefully applied to diagnosis of atypical phenylketonuria, dystonia, Parkinson's disease, Alzheimer's disease, depression, autism, schizophrenia, vitiligo, or endothelial dysfunctions.

DESCRIPTION OF DRAWINGS

FIG. 1A is HPLC chromatograms of the products obtained from the tetrahydrobiopterin-reaction mixtures under the enzyme-free condition. FIG. 1B is HPLC chromatograms of biopterin-glucosides produced by BGluT. FIG. 1C is HPLC chromatograms obtained by adding 1 µM of dihydrobiopterin to the same mixture for enzyme reaction as in FIG. 1B and then oxidizing under acidic condition.

FIG. 4 (insert) shows comparison between biopterins originated from the dihydrobiopterin in the same reaction mixture (X-axis) and biopterins obtained by oxidizing the same concentrations of dihydrobiopterin without enzyme reaction (Y-axis).

BEST MODE

The present invention provides a method for simultaneous quantitative analysis of both tetrahydrobiopterin and its oxidized forms (i.e., dihydrobiopterin and biopterin) in a sample, which comprises:

(a) adding a sample to an enzyme solution comprising a protein selected from the group consisting of proteins as set forth in SEQ ID NOs: 1 to 5 and UDP-glucose or UDP-xylose and then performing an enzymatic reaction;

(b) oxidizing the reaction mixture obtained in Step (a) and then measuring each amount of biopterin and biopterin-glycoside product; and (c) obtaining an amount of tetrahydrobiopterin from the amount of biopterin-glycoside product obtained from Step (b), using a calibration curve between biopterin and biopterin-glycoside product.

The protein as set forth in SEQ ID NO: 1 (i.e., BGluT) is a recombinant protein produced from the gene isolated from genome of bacteria belonging to the genus *Synechococcus* and has a pteridine glucosyltransferase activity (Chung H J, Kim Y, Kim Y J, Choi Y K, Hwang Y K, Park Y S (2000) Purification and characterization of UDP-glucose:tetrahydrobiopterin glucosyltransferase from *Synechococcus* sp. PCC 7942. Biochim. Biophys. Acta 1524, 183-188; and Choi Y K, Hwang Y K, Park Y S (2001) Molecular cloning and disruption of a novel gene encoding UDP-glucose:tetrahydrobiopterin alpha-glucosyltransferase gene in *Synechococcus* sp. PCC 7942. FEBS Lett. 502, 73-78). The proteins as set forth in SEQ ID NOs: 2 to 5 are newly isolated proteins according to the present invention. It is newly found in the present invention that they have also a pteridine glycosyltransferase activity, even though they have only about 50% of identity with BGluT.

In the analytical method of the present invention, the sample is a sample for biomedical research or a biological sample. The biological sample includes, but not limited to, blood (plasma and/or serum), urine, cerebrospinal fluid, and cell lysate (e.g., hepatocyte lysates or cultured cell lysates), which are originated from a mammal (such as human). Preferably, the biological sample may be a human blood or urine.

In the analytical method of the present invention, the amounts of the protein selected from the group consisting of proteins as set forth in SEQ ID NOs: 1 to 5; and the substrate (i.e., UDP-glucose or UDP-xylose) may be controlled, according to the samples analyzed. Since the concentration of tetrahydrobiopterin in biological samples is not more than 1 µM in general, the amount of protein may be in the range of 0.01 to 5 µg/100 µl, preferably 0.5 to 1 µg/100 µl; and the amount of UDP-glucose or UDP-xylose may be in the range of 50 to 500 µM, preferably 250 to 500 µM. However, the amounts are not limited thereto.

Figure 3:
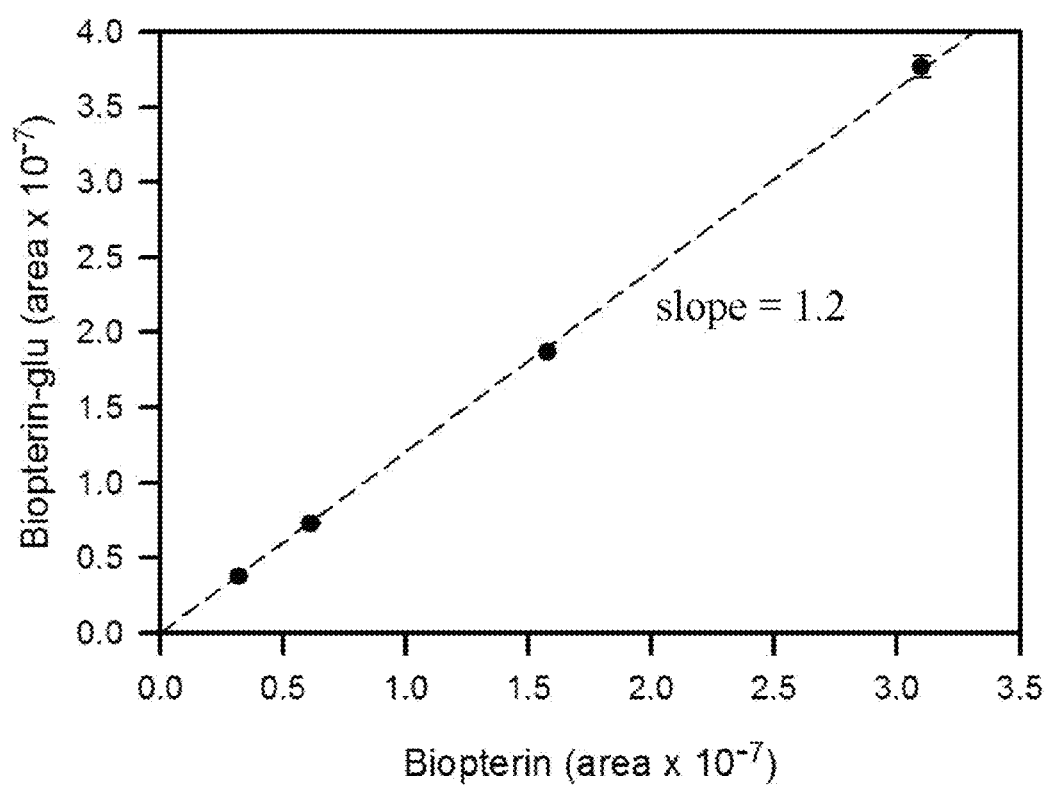
FIG. 3 shows a stoichiometry of BGluT reaction according to the concentrations of tetrahydrobiopterin. The biopterin of X-axis is a value obtained by oxidizing the reaction mixture having 0.1-1 µM of tetrahydrobiopterin without enzyme reaction. Y-axis is a peak area of biopterin-glucoside obtained by incubating the same reaction mixture with BGluT and then oxidizing the resulting mixture. The regression line obtained using SigmaPlot program has 1.2 of slope.

And also, the enzyme reaction solution further comprises a metal ion in order to facilitate the enzyme reaction. The metal ion may be selected from the group consisting of $Mg^{2+}$, $Ca^{2+}$, and $Mn^{2+}$, preferably $Mg^{2+}$ ion (e.g., $MgCl_2$). The amount of the metal ion may be also controlled according to types and expected amounts of the sample analyzed. And also, the enzyme solution further comprises an antioxidant, e.g., ascorbic acid, in order to inhibit potential oxidation of tetrahydrobiopterin in a sample, during the analysis. The amount of the antioxidant may be also controlled according to types and expected amounts of the sample analyzed. For example, when the sample is a biological sample such as blood or urine, the enzyme solution may comprise 0.1 to 1 µg/100 µl of the protein selected from the group consisting of proteins as set forth in SEQ ID NOs: 1 to 5; 50 to 500 µM of UDP-glucose or UDP-xylose; 1 to 10 mM of a metal ion selected from the group consisting of $Mg^{2+}$, $Ca^{2+}$, and $Mn^{2+}$; and 0.04 to 0.4 w/w % of ascorbic acid, in phosphate-buffered saline or 10 to 100 mM of Tris-HCl buffer. Preferably, the enzyme solution may comprise 0.5 to 1 µg/100 µl of the protein selected from the group consisting of proteins as set forth in SEQ ID NOs: 1 to 5; 250 to 500 µM of UDP-glucose or UDP-xylose; 10 mM of a metal ion selected from the group consisting of $Mg^{2+}$, $Ca^{2+}$, and $Mn^{2+}$; and 0.05 w/w % of ascorbic acid, in phosphate-buffered saline or 50 mM of Tris-HCl buffer. More preferably, Tris-HCl buffer may be used as a buffer medium, so as to avoid potential precipitation during the enzyme reaction. The pH of the enzyme solution may be, but not limited to, pH 7 to 8, preferably about pH 7.5. The enzyme reaction may be performed for not more than about 1 hour, according to the amounts of the enzyme and reaction temperatures. It was found in the present invention that the enzyme reaction may be completed at about 37° C. (normal body temperature) within 20 minutes, preferably for 5 to 20 minutes. That is, it was found that, when 1 µg of the enzyme is used for 100 µl of the reaction mixture having 1 µM of tetrahydrobiopterin, the enzyme reaction can be completed within 10 minutes (see FIG. 3). The reaction time may be more reduced by increasing the amount of the enzyme used.

Each amount of biopterin and biopterin-glycoside product may be measured by oxidizing the reaction mixture obtained in Step (a) and then performing high performance liquid chromatography (HPLC). The oxidation may be performed through iodine oxidation. For example, if iodine oxidation is used, an acidic iodine solution may be added to the enzyme reaction mixture to oxidize the oxidized forms of tetrahydrobiopterin (i.e., dihydrobiopterin and biopterin) into biopterin; and to oxidize the tetrahydrobiopterin-glycoside product into biopterin-glycoside product; and then each amount may be analyzed by one-time measurement (i.e., single measurement), using HPLC fluorescence detector. That is, the amount of biopterin [i.e., product of iodine-oxidation reaction of the oxidized forms of tetrahydrobiopterin (dihydrobiopterin and biopterin)] and the amount of biopterin-glycoside product may be analyzed by oxidizing the reaction mixture obtained in Step (a) with an acidic iodine solution; and then measuring each amount of biopterin and biopterin-glycoside product using a single fluorometric high performance liquid chromatography.

The acidic iodine solution may be prepared by dissolving potassium iodide (KI) in a concentration of 1.8 to 2.2% and iodine ($I_2$) in a concentration of 0.9 to 1.1%, in 0.9 to 1.1 M of HCl solution. The HPLC may be performed with a conventional column, such as C18 column.

Figure 2:
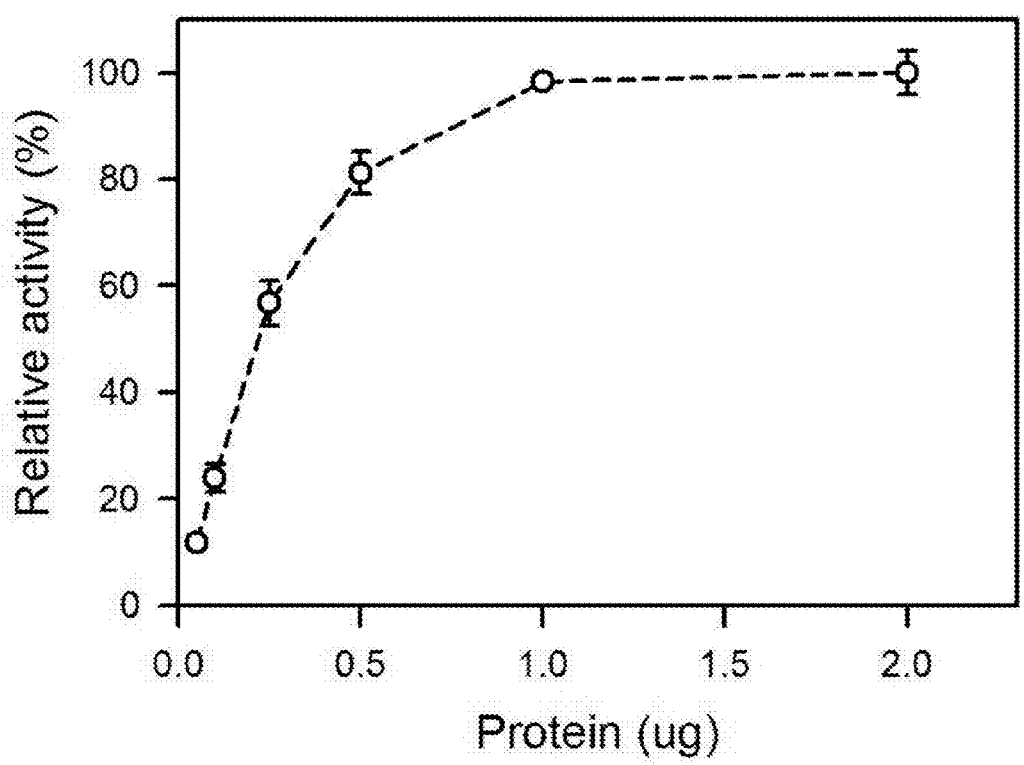
FIG. 2 shows a production profile of tetrahydrobiopterin-glucoside according to the amounts of BGluT.

The amount of tetrahydrobiopterin may be measured, using a calibration curve between biopterin and biopterin-glycoside product, which can be obtained from each peak areas thereof in HPLC chromatogram. That is, since all of the tetrahydrobiopterin are converted to tetrahydrobiopterin-glycoside product under the condition of enzyme reaction, quantitative relationship may be obtained by comparing the HPLC peak area of biopterin-glycoside product obtained from oxidation product with the HPLC peak area of biopterin obtained from non-enzyme treated oxidation product. According to the experiment of the present inventor, biopterin and its glycosylated product showed nearly perfect linear-proportional relationship. For example, the ratio thereof was 1:1.2, when a calibration curve was obtained using the HPLC peak areas of biopterin obtained by oxidizing 100 l of mixture having 50 mM Tris-HCl (pH 7.5), 10 mM $MgCl_2$, 0.05% ascorbic acid, 500 µM UDP-glucose, and 0.1-1 µM tetrahydrobiopterin; and the HPLC peak areas of biopterin-glucose product obtained by adding 1 µg of BGluT to the same mixtures and then oxidizing the resulting mixtures (see FIG. 2). The florescence used was in 350 nm/450 nm (excitation/emission). Under the florescence condition, biopterin-glucose of the same concentration show 1.2 times higher peak area than biopterin. Therefore, when analysis is performed under the condition, the concentration of tetrahydrobiopterin in a sample may be obtained by dividing the amount of glycosylated product by 1.2. When other florescence conditions are used, the ratio may be determined through a separate experiment. In addition, in case of using another glycosylated product such as biopterin-xylose, the ratio may be also determined through a separate experiment.

The present invention also provides a method for selective quantitative analysis of tetrahydrobiopterin in a sample, which comprises:

(a') adding a sample to an enzyme solution comprising a protein selected from the group consisting of proteins as set forth in SEQ ID NOs: 1 to 5 and UDP-glucose or UDP-xylose and then performing an enzymatic reaction; and (b') measuring an amount of a glycosylated product of tetrahydrobiopterin in the reaction mixture obtained in Step (a').

Step (a') may be performed according to the same methods as in Step (a).

In Step (b'), the amount of a glycosylated product of tetrahydrobiopterin may be measured through acidic iodine oxidation and HPLC analysis. And also, in case of using a radioactive isotope or antibodies, it may be measured without oxidation thereof.

For example, if iodine oxidation is used, an acidic iodine solution may be added to the enzyme reaction mixture to oxidize the glycosylated product of tetrahydrobiopterin; and then the amount thereof may be analyzed using HPLC fluorescence detector. The acidic iodine solution may be prepared by dissolving potassium iodide (KI) in a concentration of 1.8 to 2.2% and iodine ($I_2$) in a concentration of 0.9 to 1.1%, in 0.9 to 1.1 M of HCl solution; preferably a solution obtained by dissolving potassium iodide (KI) in a concentration of 2% and iodine ($I_2$) in a concentration of 1%, in about 1 M of HCl solution. The HPLC may be performed with a conventional column, such as C18 column.

Figure 13:
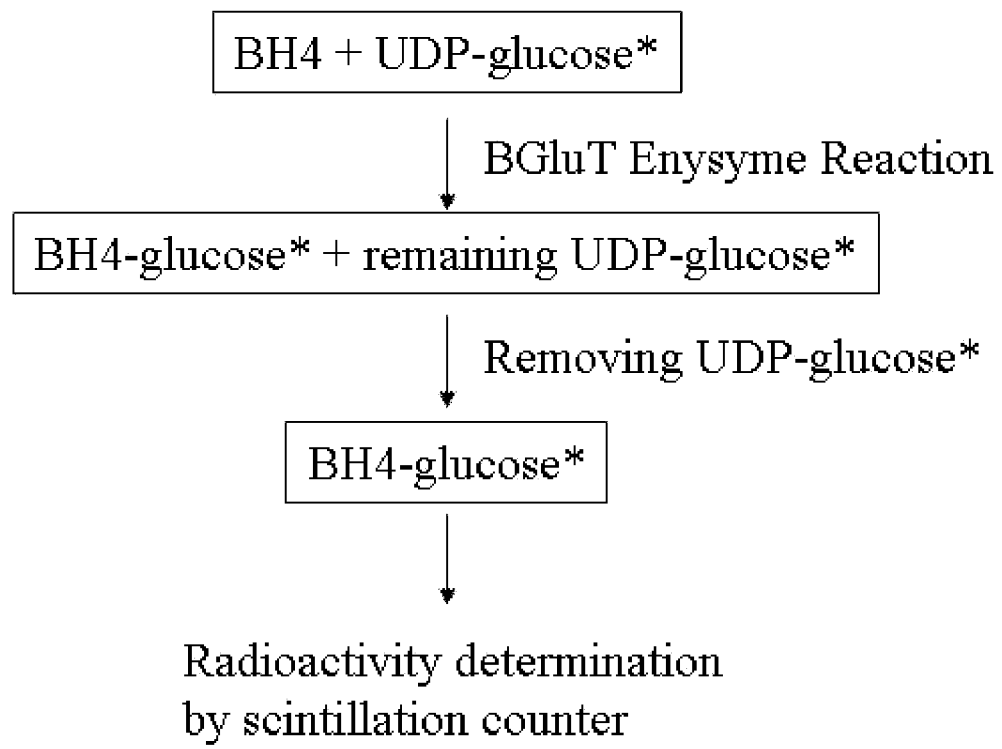
FIG. 13 shows an example for measuring tetrahydrobiopterin-glucose product using a radioactive isotope.

In case of using a radioactive isotope, the analysis may be carried out, for example, by performing the enzyme reaction with e.g., a UDP-glucose labeled with $^{14}C$-glucose, optionally removing the un-reacted UDP-glucose with, e.g., ion-exchange resin, and then measuring the amount of $^{14}C$-labeled glycosylated product by a scintillation counter using a scintillation cocktail (see FIG. 13). The $^{14}C$-labeled UDP-glucose is commercially available (for example, PerkinElmer Inc.).

Figure 14:
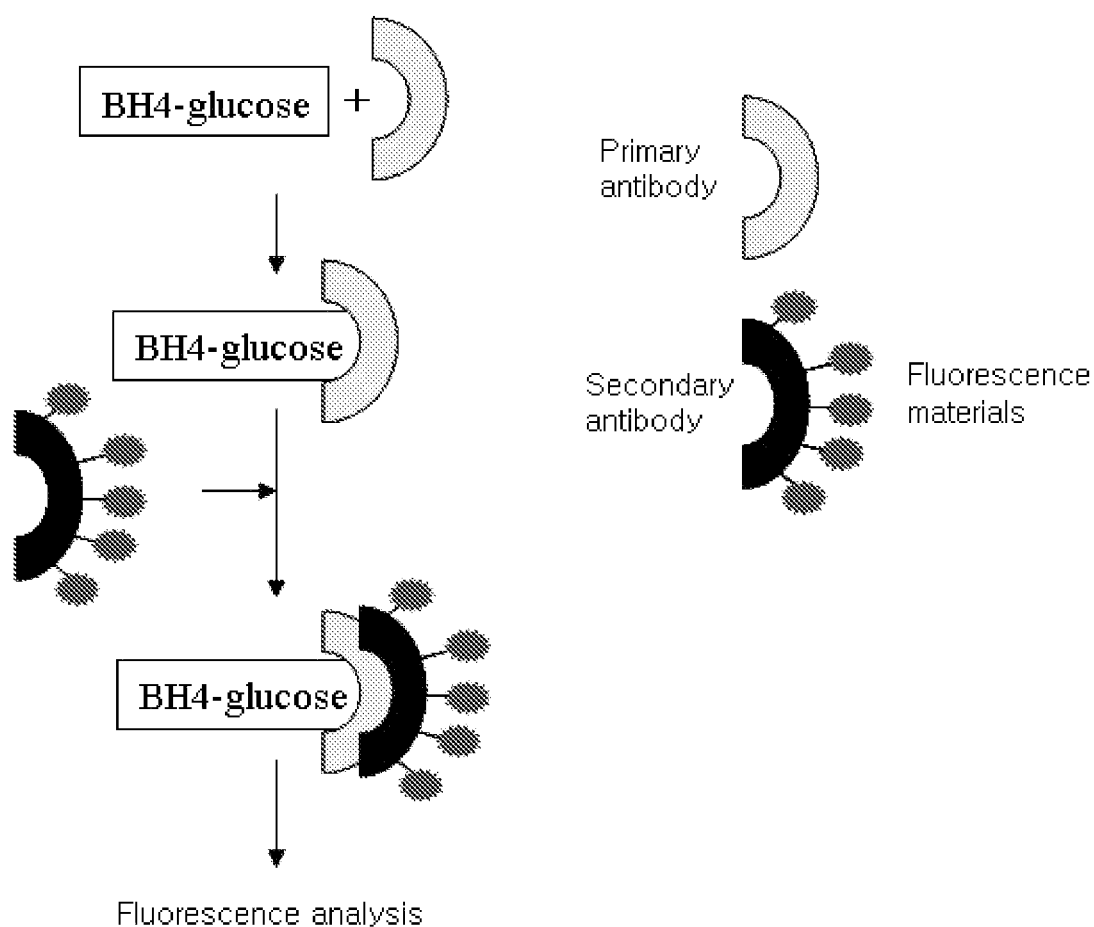
FIG. 14 shows an example for measuring tetrahydrobiopterin-glucose product using polyclonal or monoclonal antibodies.

And also, in case of using antibodies, the amount of the glycosylated product may be measured by an enzyme-linked immunosorbent assay (ELISA) using monoclonal or polyclonal antibodies against tetrahydrobiopterin-glucose or biopterin-glucose (see FIG. 14). The antibodies may be prepared from tetrahydrobiopterin-glycoside or biopterin-glycoside, using conventional methods for preparing monoclonal or polyclonal antibodies.

The analytical method of the present invention may be usefully applied to diagnosis of various diseases requiring the analysis of tetrahydrobiopterin, for example, atypical phenylketonuria, dystonia (especially, dopa-responsive dystonia), Parkinson's disease, Alzheimer's disease, depression, autism, schizophrenia, vitiligo, or endothelial dysfunctions.

The present invention also provides a newly found protein having pteridine glycosyltransferase activity, selected from the group consisting of proteins as set forth in SEQ ID NOs: 2 to 5.

Figure 8:
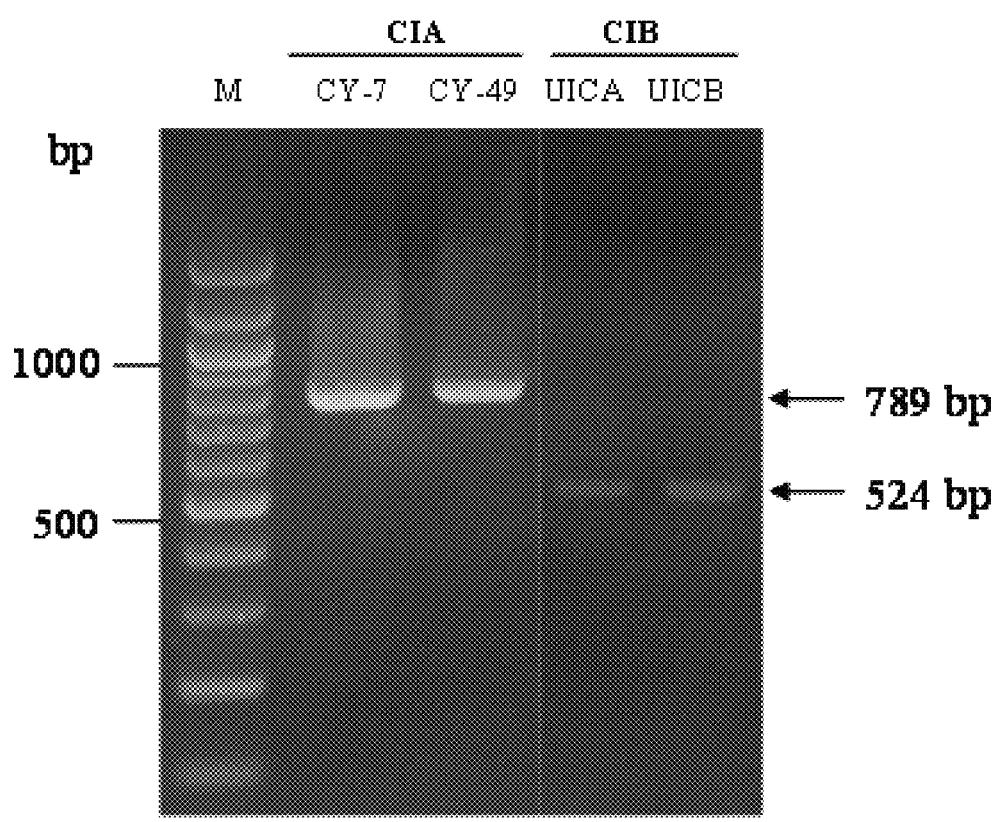
FIG. 8 shows the result of electrophoresis on 1% agarose gel of the amplified DNAs obtained by using degenerate primer sets. 789 bp of DNA product was obtained from CY-7 and CY-49 genomic DNAs. 524 bp of DNA product was obtained from UICA and UICB genomic DNAs.

Through Blast search to the NCBI microbial genomic sequences, using BGluT having pteridine glycosyltransferase activity (protein as set forth in SEQ ID NO: 1), more than 100 proteins showing about 12% or more of identity were found in various bacteria including cyanobacteria and archaebacteria. And also, through the analysis of multiple alignment and phylogenetic tree to the 94 proteins among them, it was found that the proteins of cyanobacteria were crowded in a separate group (Group C). The present inventor further divided Group C; and then designed degenerate primer sets (primer pair of SEQ ID NOs: 11 and 12 or SEQ ID NOs: 13 and 14), which have appropriate degeneracy. Using the degenerate primer pairs, PCR amplification was performed in genomic DNAs of 4 microorganisms and as a result, DNA fragments were amplified in all of the 4 microorganisms (see FIG. 8). Based on nucleotide sequences obtained from the amplified fragments, their entire genetic sequences were identified, using an inverted PCR method. Each gene was cloned into an expression vector, which was then introduced into a host cell to obtain a transformant. From the resulting transformants, 4 proteins were isolated (see FIG. 9). The isolated 4 proteins showed excellent pteridine glycosyltransferase activity, even though they have low identity with BGluT (see FIG. 10). Especially, the protein CY-7 showed more excellent activity than BGluT. The origin, SEQ ID NO (amino acid and nucleotide sequences), identity with BGluT, and substrate for glycosylation of the 4 proteins are summarized in Table 1.

TABLE 1

| Origin | SEQ ID NO (amino acid) | SEQ ID NO (base) | Identity (%) | Substrate for glucosylation |
|---|---|---|---|---|
| Spirulina platensis CY-7 | 2 | 7 | 51.5 | Glucose |
| Spirulina maxima CY-49 | 3 | 8 | 51.0 | Xylose |
| Unidentified cyanobacteria sp. | 4 | 9 | 53.9 | Glucose |
| Unidentified cyanobacteria sp. | 5 | 10 | 54.2 | Glucose |

Therefore, the present invention provides a protein having pteridine glycosyltransferase activity, selected from the group consisting of proteins as set forth in SEQ ID NOs: 2 to 5.

And also, the present invention provides a polynucleotide encoding a protein having pteridine glycosyltransferase activity, selected from the group consisting of proteins as set forth in SEQ ID NOs: 2 to 5, preferably the polynucleotide selected from the group consisting of polynucleotides as set forth in SEQ ID NOs: 7 to 10.

The present invention also includes a vector comprising the polynucleotide. As a cloning vector, various conventional vectors such as pGEM T-easy (Promega Inc., USA) may be used. As an expression vector, pET28a (Novagen Inc., Germany) or pET15b (Novagen Inc., Germany) may be used. The vector may be prepared by inserting the gene encoding the polynucleotide into a cloning vector or an expression vector cleaved with appropriate restriction enzymes, according to conventional methods.

The present invention also includes a transformant obtained by transforming a host cell with the vector. The host cell is not limited, if the proteins (i.e., proteins as set forth in SEQ ID NOs: 2 to 5) can be effectively expressed. For example, a microorganism belonging to the genus Escherichia (e.g., E. coli bl21(de3), E. coli bl11(de3) pLySss, or the like) may be used as a preferable host cell.

The present invention also provides degenerate primer pairs, i.e., primer pair of SEQ ID NOs: 11 and 12; or primer pair of SEQ ID NOs: 13 and 14. The primer pairs may be used for amplifying gene segments encoding a protein having pteridine glycosyltransferase activity, through PCR reaction.

The present invention will be described in further detail with reference to the following examples. These examples are for illustrative purposes only and are not intended to limit the scope of the present invention.

EXAMPLE 1

Simultaneous Quantitative Analysis for Tetrahydrobiopterin and its Oxidized Form 1. Materials and Methods
(1) Purification of Proteins as Set Forth in SEQ ID NO: 1 (BGluT)

According to the present inventor's article (Y. K. Choi, Y. K. Hwang, Y. S. Park, Molecular cloning and disruption of a novel gene encoding UDP-glucose:tetrahydrobiopterin alpha-glucosyltransferase gene in Synechococcus sp. PCC 7942. FEBS Lett. 502 (2001) 73-78), the BGluT gene cloned in pET-28a was overexpressed in Escherichia coli strain BL21(DE3). The recombinant BGluT was homogeneously purified with Ni-NTA column (Qiagen). Briefly, the transformed E. coli was induced to overexpress the protein with 0.3 mM isopropyl thiogalactoside (IPTG). After being incubated at 37° C. for 3 hours, the harvested cells were washed with lysis buffer (50 mM sodium phosphate (pH 8.0), 300 mM NaCl, 10 mM imidazole), resuspended in the same buffer, and disrupted by sonication. The crude extract obtained after centrifugation was applied to a column of Ni-NTA gel (Qiagen) and purified according to the product manual. The recombinant BGluT protein was eluted with 250 mM imidazole in the lysis buffer. The purified protein was dialyzed against 20 mM Tris-HCl (pH 7.5), mixed with glycerol to a concentration of 30% (v/v), and stored in aliquots at −70° C. until use. The protein was stable up to 4 months. Protein concentration was determined using Bradford reagent.

(2) Preparation of Samples

Human urine was collected in 1 mM DTT (dithiothreitol) solution. The mouse liver was homogenized in 50 mM Tris-HCl (pH 7.5) and centrifuged at 13,000 rpm for 10 minutes to obtain the supernatant.

(3) Standard Reaction Conditions of BGluT Assay

Unless otherwise specified, the following standard reaction conditions were used for the determination of tetrahydrobiopterin and its oxidized forms. Reactions were carried out in a final volume of 100 µl, which consisted of 50 mM Tris-HCl (pH 7.5), 10 mM $MgCl_2$, 0.05% ascorbic acid, 500 µM UDP-glucose, 1 µg of BGluT, and an aliquot of pteridines or tissue extracts. The reaction mixture was incubated for 20 minutes at 37° C. and then mixed with 30 µl of acidic iodine solution (2% KIM % $I_2$ in 1 N HCl). After 1 hour in the dark at room temperature, the oxidized mixture was centrifuged. The supernatant was mixed with 10 µl of 5% ascorbic acid and then neutralized with 30 µl of 1 N NaOH for injection to HPLC.

(4) HPLC Analysis

The HPLC system consisted of Gilson 321 pump, Gilson 234 autoinjector, a fluorescence detector (Schimadzu RF-10AXL), and a system software (Gilson Unipoint version 5.11). Chromatography was performed on a guard column (10 μm, 4.3 mm×1 cm) and an Inertsil ODS-3 (5 μm, 150×2.3 mm, GL Science, Japan) equilibrated with 10 mM potassium phosphate buffer (pH 6.0) at room temperature. Pteridines were eluted isocratically at a flow rate of 1.2 ml/min and monitored at 350/450 nm (excitation/emission). Pteridine peaks were identified and quantified using authentic pteridines, which were purchased from Dr. B. Schirck's Lab (Jona, Switzerland). Biopterin-glucoside was isolated from *Synechococcus* sp. PCC 7942 (Y. K. Choi, Y. K. Hwang, Y. H. Kang, Y. S. Park, Chemical structure of 1-O-(L-erythro-biopterin-2'-yl)-alpha-glucose isolated from a cyanobacterium *Synechococcus* sp. PCC 7942, Pteridines, 12 (2001) 121-125).

2. Results and Discussion (1) Specific Conversion of Tetrahydrobiopterin by BGluT In order to quantitatively analyze tetrahydrobiopterin through enzyme reaction by BGluT, it should be ensured that the amount of the product is linearly increased according to concentrations and time, through irreversible enzyme reaction; and that all tetrahydrobiopterin is converted to the glucoside. And also, since various materials are present and the concentration of substrate is very low in a biological sample, a desired enzyme reaction may be seriously interfered. Accordingly, the study of the enzyme reactions by BGluT was focused on these points.

Figure 1:
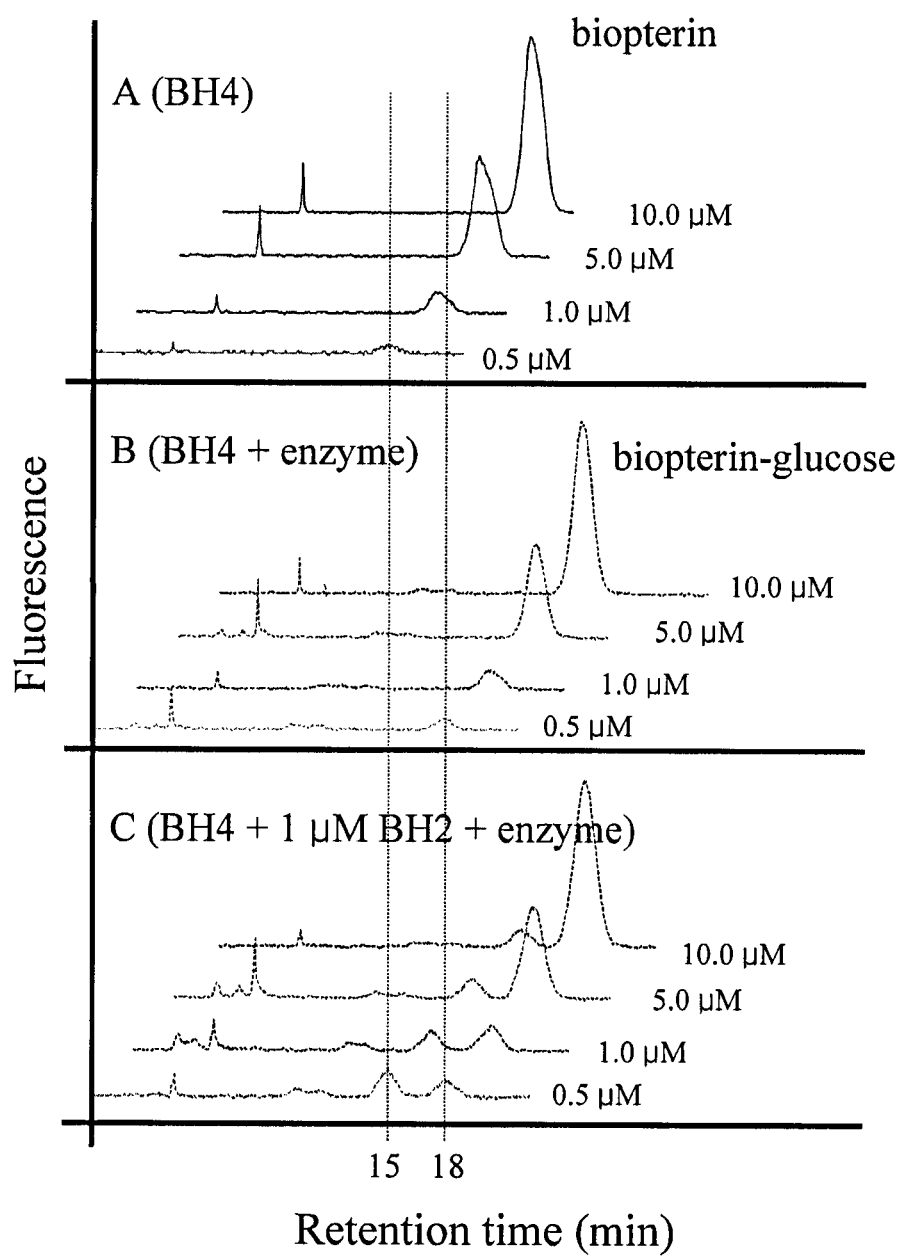
FIG. 1 shows HPLC chromatograms of the products produced from the reaction mixtures with or without the protein having tetrahydrobiopterin glucosyltransferase activity (the protein as set forth in SEQ ID NO: 1, BGluT).

To demonstrate whether BGluT glucosylates all of tetrahydrobiopterin in the reaction mixture, tetrahydrobiopterin solutions (100 μl) having predetermined concentrations were reacted with BGluT (0.15 μg) at 37 for 1 hour and then oxidized. The results obtained from quantitative analysis by HPLC are shown in FIG. 1.

FIG. 1A is HPLC chromatograms of the products obtained by oxidizing tetrahydrobiopterins under acidic condition without enzyme reaction. The biopterins oxidized from tetrahydrobiopterins were shown at elution peaks of 15 minutes. FIG. 1B is HPLC chromatograms of the products obtained by reacting the same concentrations of tetrahydrobiopterins with the enzyme and then oxidizing under acidic condition. The new peaks were shown at elution peaks of 18 minutes in all concentrations of tetrahydrobiopterins, while there is no peak in elution peaks at 15 minutes. The new peaks represent biopterin-glucosides, which are produced through oxidation of the binding product of tetrahydrobiopterin and glucose. These results show that all of the tetrahydrobiopterin is completely glucosylated through enzyme reaction, and therefore that tetrahydrobiopterin can be analyzed quantitatively from its glucosylated product.

To determine whether the presence of dihydrobiopterin, structurally similar to tetrahydrobiopterin, interferes with glucosylation of tetrahydrobiopterin, 1 μM of dihydrobiopterin was added to the same mixture for enzyme reaction as in FIG. 1B, which was then oxidized under acidic condition. As a result of analysis, there is no significant difference in the amounts of glucosylated products of tetrahydrobiopterin; and the same height of biopterin peaks were detected in all of the products (see FIG. 1C). Therefore, it is evident that BGluT can specifically convert only all of tetrahydrobiopterin to its glucosylated product, even in the presence of dihydrobiopterin.

(2) Establishment of Reaction Condition for BGluT Analysis

The results of FIG. 1 illustrate that a selective and quantitative analysis of tetrahydrobiopterin is possible using BGluT. In order to validate the possibility quantitatively, various studies were carried out to establish a standard reaction condition suitable for analysis of biological samples. In the prior art (i.e., Y. K. Choi, Y. K. Hwang, Y. S. Park, Molecular cloning and disruption of a novel gene encoding UDP-glucose:tetrahydrobiopterin alpha-glucosyltransferase gene in *Synechococcus* sp. PCC 7942. FEBS Lett. 502 (2001) 73-78), optimal reaction conditions of the native BGluT were studied. Therefore, the current studies were focused on optimal amounts of the protein for determining tetrahydrobiopterin in animal tissues within a short time. Since an analysis of tetrahydrobiopterin was usually carried out with a 100 μl reaction volume containing tissue homogenates (animal samples, except urine, were known to contain biopterins at concentrations of less than 1 μM), BGluT reaction was conducted in 100 μl of a reaction mixture containing 1 μM of tetrahydrobiopterin. When incubated for 10 minutes with increasing amounts of BGluT, the product is not increased any more if more than 1 μg of BGluT was used (see FIG. 2). Therefore, it can be concluded that an incubation at 37° C. for 20 minutes is sufficient when 1 μg of BGluT is used per 100 μl of a reaction volume. The proposed method is described as a standard reaction condition in Material and Methods. Of course, the time for reaction can be shortened to a few minutes if BGluT of more than 1 μg is used.

(3) Identification of Quantitative Relationship for BGluT Reaction

In order to critically identify the quantitative relationship between biopterin and the corresponding biopterin-glucoside as shown in FIGS. 1A and 1B, the same reactions were performed with the reaction mixture having tetrahydrobiopterin of less than 1 μM. The reaction conditions were the same as the established standard reaction condition. From the peak areas of biopterin and the corresponding biopterin-glucoside which were obtained from triplicate assays, means±standard deviations were calculated and then plotted against each other, so as to yield 1:1.2 ratio between biopterin and biopterin-glucoside (see FIG. 3). The deviation from 1:1 ratio might originate from difference in their absorption spectra. The results suggested that tetrahydrobiopterin can be fully recovered as its glucoside via BGluT assay and that the peak area of biopterin-glucoside should be divided by 1.2 for quantifying as an equivalent of biopterin.

(4) Quantitative Analysis for Effect of Dihydrobiopterin on BGluT Reaction

Biological samples contain tetrahydrobiopterin as well as its oxidized forms (dihydrobiopterin and bipterin). In order to quantitatively analyze only tetrahydrobiopterin selectively using BGluT, the BGluT reaction should be specific to tetrahydrobiopterin, without being interfered by its oxidized forms. Using various pteridines (dihydrobiopterin, biopterin, neopterin, tetrahydroneopterin, and isomers thereof) as a substrate, potential inhibitory effect was evaluated. As a result, only dihydrobiopterin among the pteridines showed a small amount of glucosylated product when the concentration was increased to 5 μM (data not shown), which is much higher than the amount actually encountered in animal tissues. It therefore was suspected that dihydrobiopterin might function as a competitive inhibitor in glucosylation of tetrahydrobiopterin by BGluT.

Figure 4:
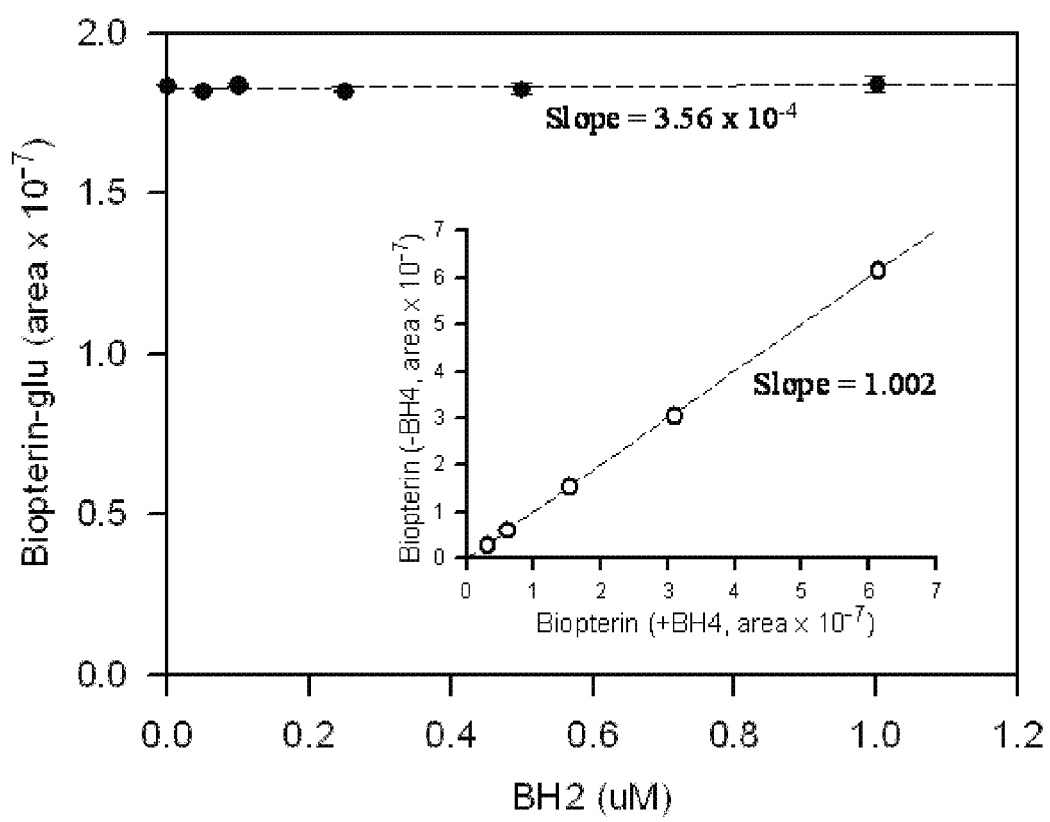
FIG. 4 shows the results obtained by examining whether dihydrobiopterin interferes with the BGluT reaction. Y-axis represents peak areas of biopterin-glucoside produced from the reaction with BGluT, increasing to fourfold higher concentrations of dihydrobiopterin (X-axis) than tetrahydrobiopterin.

The results of FIG. 1C showed that dihydrobiopterin had no influence on glucosylation of tetrahydrobiopterin by BGluT. However, when the concentration of dihydrobiopterin is higher than tetrahydrobiopterin, dihydrobiopterin could show inhibitory effects. In order to examine whether dihydrobiopterin interferes with the BGluT reaction, dihydrobiopterin was coincubated under the standard reaction condition with a fixed amount (0.25 μM) of tetrahydrobiopterin, along with increasing concentrations of dihydrobiopterin up to 4-fold (0.05~1 μM) (see FIG. 4). In FIG. 4, the X-axis represents concentrations of dihydrobiopterin added to the reaction solution and the Y-axis represents peak areas of the glucosylated product produced from tetrahydrobiopterin. The results thereof show means±standard deviations of the peak areas of biopterin-glucoside, which were obtained from triplicate assays. The slope obtained from regression line was almost zero, proving that dihydrobiopterin does not have obvious interference on the BGluT reaction, even in the presence of much higher amount of dihydrobiopterin than tetrahydrobiopterin. In general, the concentrations of the oxidized forms of tetrahydrobiopterin in a biological sample are not higher than that of tetrahydrobiopterin.

In order to examine whether the added dihydrobiopterin has been glucosylated even in small amount, the peak areas of biopterin originated from the dihydrobiopterin (X-axis) were compared with those determined from the same concentration of dihydrobiopterin without enzyme reaction (Y-axis) (FIG. 4 (insert)). The slope obtained from regression line was almost 1. These results strongly support that dihydrobiopterin at the level of physiological concentrations is not glucosylated by BGluT and that it does not have any interference on the enzyme reaction.

(5) Validation of BGluT Assay Using Animal Samples

Figure 5:
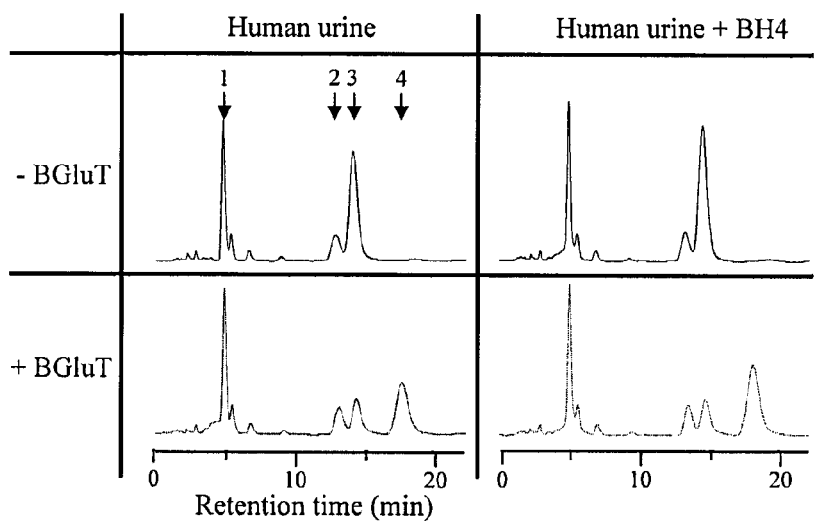
FIG. 5 shows chromatograms of BGluT assays using human urine. The arrows represent the eluting positions of (1) neopterin, (2) pterin, (3) biopterin, and (4) biopterin-glucoside, respectively.

The validity of the BGluT method was evaluated in human urine, which are easily available and known to contain tetrahydrobiopterin. The assay was performed in triplicate for the purpose of quantitative analysis under the same conditions. The peak areas of biopterin and its glucosylated product were measured and the obtained results were summarized in Table 2. Chromatograms were also presented in FIG. 5. Total biopterin was determined separately by analyzing the reaction mixture which was not incubated with BGluT. When the reaction mixture incubated with BGluT was analyzed by HPLC, biopterin-glucoside appeared in the chromatogram, whereas a corresponding amount of biopterin disappeared. When authentic tetrahydrobiopterin was added to the reaction mixture, the increased amounts of total biopterin or biopterin-glucoside were coincided well with each other as well as with those determined from the separate assay of authentic tetrahydrobiopterin. However, the residual biopterins after BGluT assay remained constant. That is, these results show that the added tetrahydrobiopterin was completely converted to biopterin-glucoside. The full recovery of added tetrahydrobiopterin as biopterin-glucoside supports that all the indigenous tetrahydrobiopterin in a sample would have been converted to biopterin-glucoside. Since the total biopterin determined from the non-enzymatic reaction mixture should be equal to the sum of residual biopterin and biopterin-glucoside obtained by BGluT assay, the present inventor compared them in the last column of Table 2. The ratios were close to 1, validating the BGluT assay results.

TABLE 2

Validation of the BGluT assay using human urine[a]

| | BGluT | Biopterin (peak area × $10^{-7}$) | Biopterin (peak area × $10^{-7}$) | Total Biopterin ratio (−BGluT/+BGluT)[d] |
|---|---|---|---|---|
| Urine | − | 4.37 ± 0.14 | ND[b] | 4.37/(1.56 + 2.49) = |
| | + | 1.56 ± 0.08 | 2.49 ± 0.10 (2.99)[c] | 1.08 |
| Urine + tetrahydrobiopterin | − | 5.29 ± 0.14 | ND | 5.29/(1.62 + 3.35) = |
| | + | 1.62 ± 0.10 | 3.35 ± 0.04 (4.02)[c] | 1.06 |
| tetrahydrobiopterin | − | 0.85 ± 0.0. | ND | 0.85/0.86 = |
| | + | ND | 0.83 ± 0.11 (1.03)[c] | 0.99 |

Figure 6:
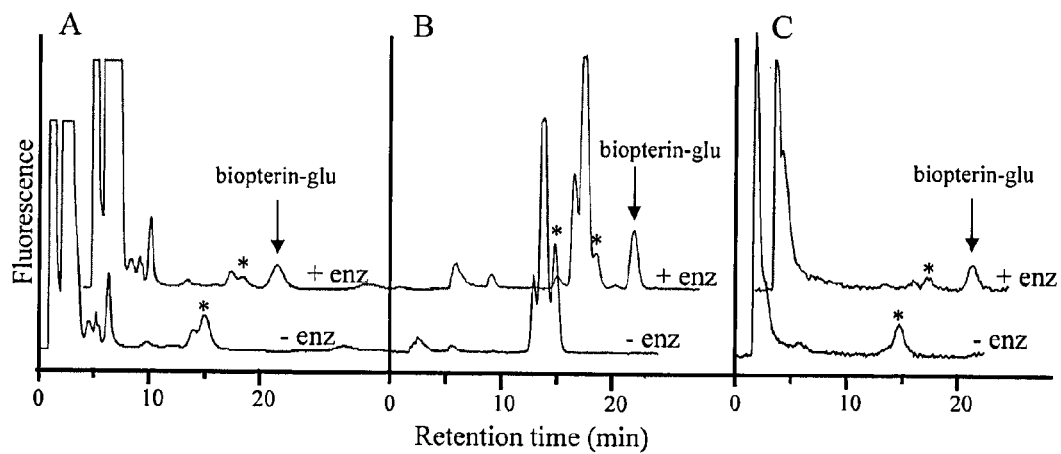
FIG. 6 shows chromatograms of BGluT assays using various animal samples. Using the standard reaction conditions, (A) human plasma, (B) mouse liver extract, and (C) rat plasma were assayed either with BGluT (+enz) or without BGluT (−enz).

[a]Based on triplicate assays of human urine, which was taken one time. 10 µl was used for the reaction and the reaction conditions are the same as in the above. Data are means ± standard deviations.
[b]Not detected
[c]Normalized values to the equivalent of biopterin by dividing the original values in parenthesis by 1.2
[d]The total biopterin from enzyme-free reaction was divided by the sum of biopterin and biopterin-glucoside obtained from the enzyme reaction In order to examine whether BGluT assay can be affected by complex biological constituents, BGluT assay was further assessed using human and rat plasma and mouse liver extract (FIG. 6). Although 90 µl of human blood was included in the 100 µl reaction mixture (since the concentration of tetrahydrobiopterin was very low therein), there was no interference in the enzyme reaction. Although not shown statistically, the peak areas of total biopterin were coincided well with those of residual biopterin plus biopterin-glucoside (data not shown). These results support that BGluT assay may be applied to any biological samples.

(6) Conclusion

The present inventor have developed a new method for the simultaneous determination of both tetrahydrobiopterin and its oxidized forms (dihydrobiopterin and biopterin) in a biological sample, the method of which includes BGluT-catalyzed glucosylation reaction and acidic iodine oxidation followed by single fluorescence HPLC. Using authentic tetrahydrobiopterin and animal samples, the present inventor demonstrated that BGluT was selective to tetrahydrobiopterin and not affected by oxidized forms, thereby converting all of tetrahydrobiopterin in the mixture of reduced and oxidized forms. The stoichiometric yield of tetrahydrobiopterin-glucoside from tetrahydrobiopterin was also confirmed by comparing the peak areas of the equimolar amounts of biopterin and biopterin-glucoside, which were determined to be 1:1.2. Therefore, a single chromatography was shown to be enough for quantifying tetrahydrobiopterin and its oxidized forms in a sample.

Compared to the currently available methods, the BGluT assay provides several advantages. Owing to the simplified HPLC procedure, the BGluT method would save time and labor, thereby reducing the risk of experimental errors. The BGluT assay may not be susceptible to the conditions required for conventional enzyme reaction (e.g., temperature, time, and compositions of reactants), because the reaction goes to completion when all of tetrahydrobiopterin in the reaction mixture are exhausted. This means that BGluT assay ensures to obtain the same results even if the reaction temperature and/or the amount BGluT are changed depending on experimental conditions. Finally, BGluT assay have an advantage for stock of reagents. Tetrahydrobiopterin in a sample may be easily oxidized under the long term of storage, which makes an accurate determination difficult. However, once the sample is stored after reaction with BGluT, the same result can be obtained because biopterin-glucoside maintains intact, even during the oxidation.

EXAMPLE 2

Separation of Novel Proteins and Evaluation of their Activities

1. Materials and Methods
(1) Strains, Genomic DNA and Vector

*Spirulina platensis* CY-7 (referred to "CY-7", hereinafter) and *Spirulina maxima* CY-49 (referred to "CY-29", hereinafter) were provided from Korea Marine Microalgae Culture Center (KMCC). The unidentified wild cyanobacteria A (referred to "UICA", hereinafter) and B (referred to "UICB", hereinafter) were collected in a branch of the Nakdong Rive in Korea. *E. coli* Top 10F' was used as a host cell for a gene-recombinant plasmid and *E. coli* BL21 (DE3) was used as a host cell for expression of the recombinant protein. The pGEM T-easy vector was used as a cloning vector and pET 28a and 15b were used as an expression vector.

(2) Extraction of Genomic DNA

Genomic DNAs were extracted using DNA isolation kit (LaboPass Genomic DNA Isolation Kit, Cosmogentech Co. Ltd., Korea). The extracted DNAs were dissolved in 50 μl of TE buffer (10 mM Tris, 1 mM EDTA pH 8.0) and stored at −70° C.

(3) PCR Reaction

The composition of mixture for PCR reaction is as follows: 1× reaction buffer (10 mM Tris-HCl (pH 9.0), at 25° C., 50 mM KCl, 0.1% Triton X-100), 1.5 mM $MgCl_2$, 0.2 mM dNTPs, 0.5 pmol of each forward and reverse primers, and a template DNA. Total volume of the mixture was set to 50 μl using 2 units of Taq DNA polymerase. The PCR condition was as follows: pre-denaturation for 4 minutes at 94° C., denaturation for 1 minute at 94° C., annealing for 1 minute, and extension for 1-2 minutes at 72° C. 30 to 35 cycles of PCR were performed to amplify DNA and then terminated with final extension for 10 minutes at 72° C. The electrophoresis in 1% of agarose gel was performed to detect the amplified DNA, which was then inserted into a vector for analysis of its nucleotide sequence. Table 2 represents the degenerate primers and annealing temperatures for amplifying partial sequence of the gene encoding pteridine glycosyltransferase (PGT). Table 4 represents the primers and annealing temperatures for inverted PCR cloning. Table 5 represents the primer and annealing temperatures for expression of the recombinant protein.

TABLE 3

Degenerate primers and annealing temperatures for amplifying partial sequence of PGT

| Primer set | | Sequence | SEQ ID NO. | Degeneracy | Annealing Temp. |
|---|---|---|---|---|---|
| Set 1 | Forward | GT TCA GGA WTA GGA GGT GGA GT<br>  S   G   I/L G   G   G | 11 | 2 | 59 °C. |
| | Reverse | CGC YTC AAT WGC TAC ATT TCC A<br>  A   E   I   A   V   N   G | 12 | 4 | |
| Set 2 | Forward | AC GAC TGG CTM YCG YTT-TAY CTG A<br>  D   W   L   P/S L/F Y   L | 13 | 24 | 65 °C. |
| | Reverse | GC YTC CAC CCA YTT RGG GGT CA<br>  E   V   W   K   P   T | 14 | 8 | |

TABLE 4

Primer and annealing temperature for inverted PCR cloning

| | | | Sequence | SEQ ID NO. | Annealing Temp. |
|---|---|---|---|---|---|
| CY-7 | Outer primer | Forward<br>Reverse | ACCGGGGATTTTTGAATACAGATGAACTAC<br>GATAGGGACTCTAACACTGACCCAGAAGG | 15<br>16 | 60 °C. |
| | Inner primer | Forward<br>Reverse | GATGAACTACAACAGGGTCTGCGTC<br>CGGCTTTTTAAGGCTTTTGCCATATTC | 17<br>18 | 57 °C. |
| CY-49 | Outer primer | Forward<br>Reverse | ACAGGGTCTGCGTGAATG<br>CTCTAACACTGACCCAGAAGG | 19<br>20 | 48 °C. |
| | Inner primer | Forward<br>Reverse | GTCTGCGTGAATGTCGAGG<br>ATGACCTCGGCTGTGTAAG | 21<br>22 | 50 °C. |
| UICA UICB | Outer primer | Forward<br>Reverse | CGGGAGCCTACAAAAAGAGCTAGG<br>AATATGATCCATCGCCAAAGAAACGG | 23<br>24 | 58 °C. |
| | Inner primer | Forward<br>Reverse | CCTACAAAAAGAGCTAGGCGACTGTTTTG<br>CCAAAGAAACGGAAGCCATGCTG | 25<br>26 | 62 °C. |

Two primer sets (each having inner and outer primers) were constructed for nest PCR. For UICA and UICB, the same set was used because they have similar sequences.

TABLE 5

Primer and annealing temperature for expression of the recombinant proteins

| | Sequence | SEQ ID NO. | Annealing Temp. |
|---|---|---|---|
| CY-7 Forward | CATATGACTCCAACAAGCTGGAAATTACTATTTATATC | 27 | 65 °C. |
| Reverse | GGATCCTCAATTTTTAAGCCGGGTAACATCAGAT | 28 | |
| CY-49 Forward | CATATGCCTCAAAAAAGCTGGAAATTACTATT | 29 | 62 °C. |
| Reverse | GAATTCTTCAATTTTTAAGCGCGATCACATC | 30 | |
| UICA Forward | CATATGAGTCGAAAACTGTTATTTCTCTCCACC | 31 | 66 °C. |
| UICB Reverse | GGATCCTTATTTTTTGCGAGCAAAAATTTCTTCAA | 32 | |

The same primer set was used for UICA and UICB because they have similar nucleotide sequences.

(4) Construction of Expression Vector and Transformation

The PCR products were cloned to the pGEM T vector, which were then screed using X-gal and IPTG in ampicillin-containing media. The screened vectors were cut with the corresponding restriction enzymes to inserted sites and then the genes were recovered through gel elution. The recovered genes were inserted into the pET28b or pET15b vector using the same restriction enzymes, with which Top 10F' strains were transformed. The obtained transformed strains were screened in kanamycin/ampicillin-containing media. The insertion of each gene was identified finally through PCR and restriction enzyme treatment. The identified expression vectors were transformed into the protein expression strain BL21 (DE3) pLySs (see Table 6).

(5) Overexpression and Purification of Recombinant Protein

The transformed strains were inoculated on LB broth (Kanamycin; Km+/Ampicillin; Amp+), cultivated at 37° C. until O.D$_{600}$ become 0.6. Appropriate concentrations of IPTG were added to the media, which was then cultivated for 4 to 8 hours at 22° C. Overexpression of the recombinant protein was confirmed using 10% SDS PAGE (see Table 6).

All of the recombinant proteins were purified with Ni-NTA Agarose gel (Qiagen Inc.). The cell cultures were centrifuged at 8000 rpm for 20 minutes to obtain the cell precipitates. The cell precipitates were floated with addition of a lysis buffer (50 mM NaPO$_4$, pH 8.0, 10 mM imidazole, 300 mM NaCl) in a ratio of 100 μl per 1 ml of the media. The cells were disrupted through ultrasonic cell disruption (pulse on: 0.1 sec, pulse off: 0.1 sec) and then centrifuged at 13000 rpm, 4° C. for 30 minutes to recover the supernatants. The supernatants were passed trough 1 ml of Ni-NTA agarose gel and then poured 4 ml of a washing buffer (50 mM NaPO$_4$, pH 8.0, 10-100 mM imidazole, 300 mM NaCl) and an elution buffer (50 mM NaPO$_4$, pH 8.0, 250 mM imidazole, 300 mM NaCl) on the gel to collect 1 ml of each fractions. The recovered proteins were dialyzed with 20 mM Tris-HCl (pH 7.5) and then stored at −70° C.

The expression vectors, expression strains, and culture conditions for producing the recombinant proteins were summarized in Table 6.

TABLE 6

| Protein | Expression vector | Culture conditions |
|---|---|---|
| CY-7 | pET28b | Adding 200 μM IPTG at O.D. 0.6 and Cultivating at 22° C. for 8 hours |
| CY-49 | pET28b | Adding 50 μM IPTG at O.D. 0.6 and Cultivating at 22 for 8 hours |
| UICA | pET15b | Adding 125 μM IPTG at O.D. 0.6 and Cultivating at 22 for 4 hours |
| UICB | pET15b | Adding 125 μM IPTG at O.D. 0.6 and Cultivating at 22 for 6 hours |

(6) Analysis of Protein Activity

The protein activity was assayed in 100 μl of reaction mixture having the following composition: 50 mM Tris-HCl (pH 7.5), 10 mM MgCl$_2$, 0.2% ascorbic acid, 1 μM tetrahydrobiopterin, 500 μM UDP-glycoside (one of UDP-glucose, UDP-galactose, UDP-xylose, UDP-glucuronic acid, UDP-galacturonic acid, UDP-N-acetylglucosamine, and UDP-N-acetylgalactosamine) and an appropriate amount of the purified recombinant protein. The reaction was performed at 37 for 10-60 minutes depending on an amount of protein. 30 μl of acidic iodine solution (2%/1% KI/I$_2$ in 1 M HCl) was added to the reaction mixture and allowed in darkness for 1 hour for oxidation thereof. The mixture was centrifuged to recover the supernatant, which was then mixed with 10 μl of 5% ascorbic acid. 30 μl of 1 N NaOH was added to the resulting mixture for neutralization and then HPLC analysis was carried out.

HPLC system consisted of Gilson 321 pump, Gilson 234 autoinjector, a fluorescence detector (Schimadzu RF-10AXL), and a system software (Gilson Unipoint version 5.11). Chromatography was performed on a guard column (10 μm, 4.3 mm×1 cm) and an Inertsil ODS-3 (5 μm, 150×2.3 mm, GL Science, Japan) equilibrated with 10 mM potassium phosphate buffer (pH 6.0) at room temperature. Pteridines were eluted isocratically at a flow rate of 1.2 ml/min and monitored at 350/450 nm (excitation/emission). Pteridine peaks were identified and quantified by using authentic pteridines, which were purchased from Dr. B. Schirck's Lab (Jona, Switzerland). Biopterin-glucoside was isolated from *Synechococcus* sp. PCC 7942 (Y. K. Choi, Y. K. Hwang, Y. H. Kang, Y. S. Park, Chemical structure of 1-O-(L-erythro-biopterin-2'-yl)-alpha-glucose isolated from a cyanobacterium *Synechococcus* sp. PCC 7942, Pteridines, 12 (2001) 121-125).

(7) Characterization of Enzyme Activity

The enzymatic activities for the isolated proteins were compared with that of BGluT. First, production profiles of tetrahydrobiopterin(BH4)-glucoside produced according to amounts of the proteins was compared with that of BGluT. The enzyme activities were represented as a percentage to all converted amounts. The reaction condition was as follows. That is, reactions were performed in a final volume of 100 μl, which consisted of 50 mM Tris-HCl (pH 7.5), 10 mM $MgCl_2$, 0.05% ascorbic acid, 1 μM tetrahydrobiopterin, 500 μM UDP-glucose or UDP-xylose, and a protein (0.05-1.0 μg). The reaction mixture was incubated at 37 for 20 minutes. 30 μl of acidic iodine solution (2%/1% $KI/I_2$ in 1 M HCl) was added thereto in darkness for 1 hour at room temperature, so as to oxidize the reaction mixture. After centrifugation, the resulting supernatant was mixed with 10 μl of 5% ascorbic acid and neutralized with 30 μl of 1N NaOH for injection to HPLC.

Also, 1 μg of each protein was added to 100 μl of reaction solution containing 10 μl of human urine instead of tetrahydrobiopterin. The reaction mixture was incubated at for 20 minutes. For CY-49, 500 μM UDP-xylose was added as a substrate; and for other enzymes, UDP-glucose was added. Other reaction conditions were the same as in the above.

2. Results (1) Gene Cloning

In order to examine the presence of a gene encoding protein having pteridine glycosyltransferase activity in CY-7 and CY-49 strains whose genomic sequences are not elucidated; and the unidentified UICA and UICB, the degenerate primer sets were designed. Blast search to the NCBI microbial genomic sequences was carried out using the protein sequence of BGluT. As a result, more than 100 proteins showing about 12% or more of identity were found in various bacteria including cyanobacteria and archaebacteria. Through the analysis of multiple alignment and phylogenetic tree to the 94 proteins among them, a phylogenetic tree was obtained. The groups distinguished from the phylogenetic tree by naked eye were classified optionally as A, B, C, and D groups and each was subdivided into Group I and II. Specifically, most of the homologous proteins found in cyanobacteria were crowded in Group C.

Figure 7:
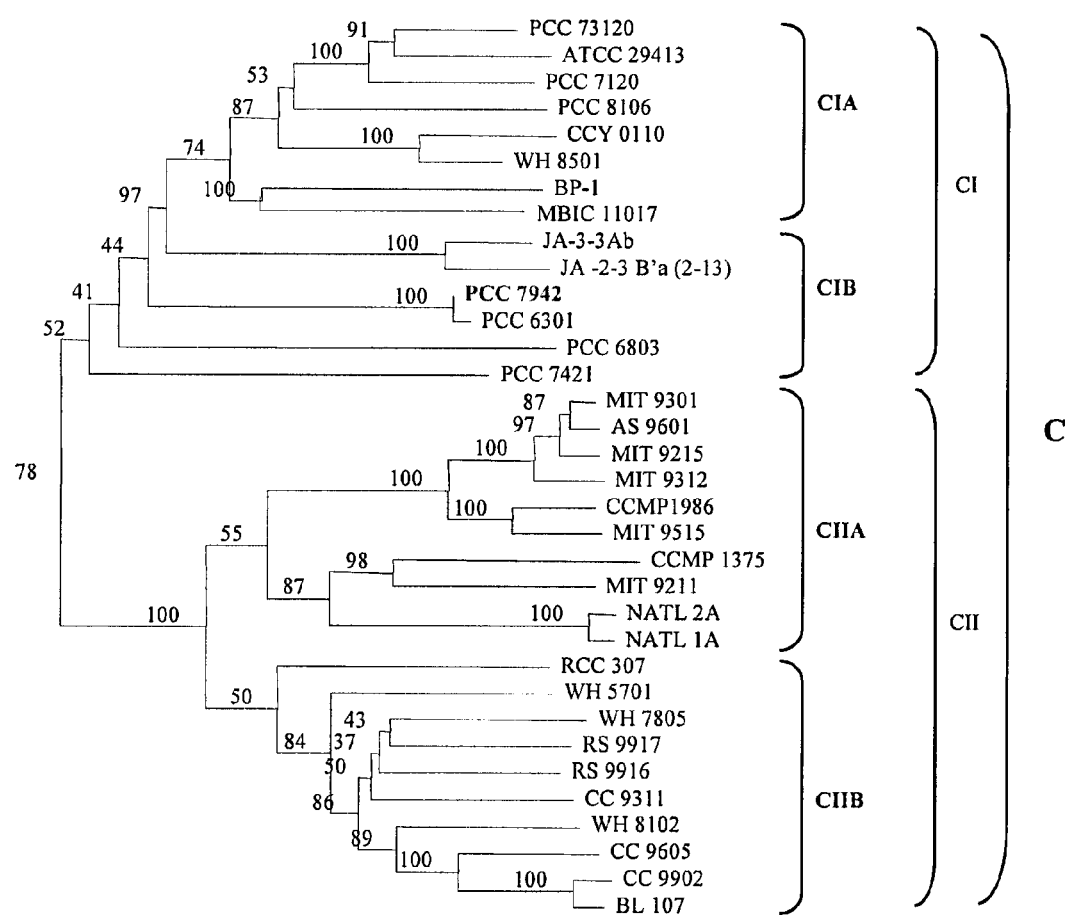
FIG. 7 shows phylogenetic tree of Group C, which was obtained by performing multiple alignment to the proteins obtained from Blast search using the amino acid sequence of BGluT.

The present inventor further divided Group C (see FIG. 7); and then designed degenerate primer sets having appropriate degeneracy, using the web server program, genefisher2. From the 3-5 primer sets screened with changing search conditions, degenerate primer sets having low degeneracy, i.e. the primer pair of SEQ ID NOs: 11 and 12 and the primer pair of SEQ ID NOs: 13 and 14 were obtained from (see Table 3).

Using the degenerate primer pairs, PCR amplification was performed in genomic DNAs of various microorganisms and as a result, DNA fragments were amplified in 4 microorganisms. That is, as a result of PCR amplification using the degenerate primer pairs, DNAs were amplified by the primer pair of SEQ ID NOs: 11 and 12 in the genomic DNAs of CY-7 and CY-49; by the primer pair of SEQ ID NOs: 13 and 14 in the genomic FNAs of UICA and UICB (see FIG. 8). The sizes of the amplified DNAs were coincided with those expected from each primer pairs.

Based on nucleotide sequences obtained from the amplified fragments, their entire genetic sequences were identified, using inverse PCR method (Triglia, T, Peterson M G, Kemp D J (1988) A procedure for in vitro amplification of DNA segments that lie outside the boundaries of known sequence. Nucleic Acids Res. 16:8186). As a result, it was confirmed that the genes have nucleotide sequences as set forth in SEQ ID NOs: 7 to 10, respectively; and that the proteins encoded by the nucleotide sequences have amino acid sequences as set forth in SEQ ID NOs: 2 to 5, respectively (see Table 1). The identities between the 4 proteins and BGluT were about 50%. However, the identity between CY-7 and CY-49 was over 90%; and the identity between UICA and UICB was 93.5%.

(2) Expression and Purification of Proteins

Figure 9:
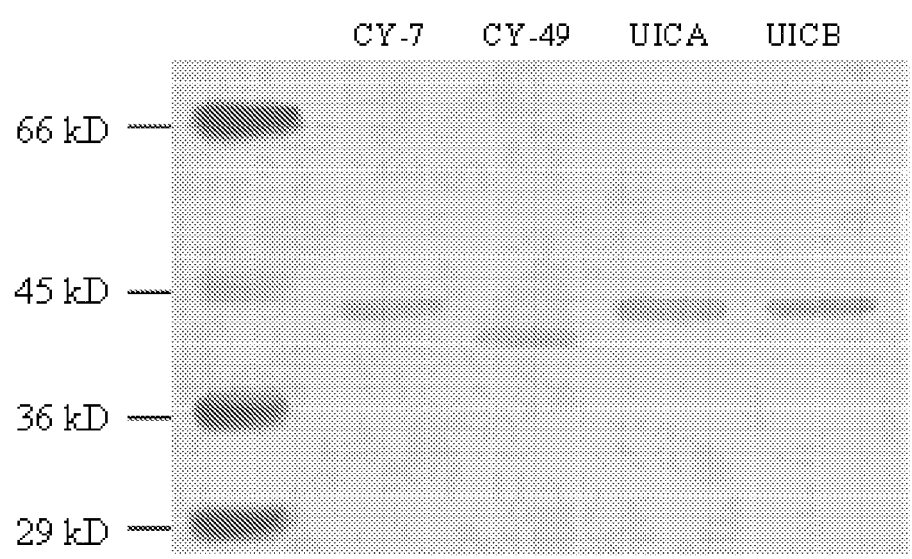
FIG. 9 shows the result of electrophoresis on SDS-PAGE gel of the purified recombinant proteins.
Figure 10:
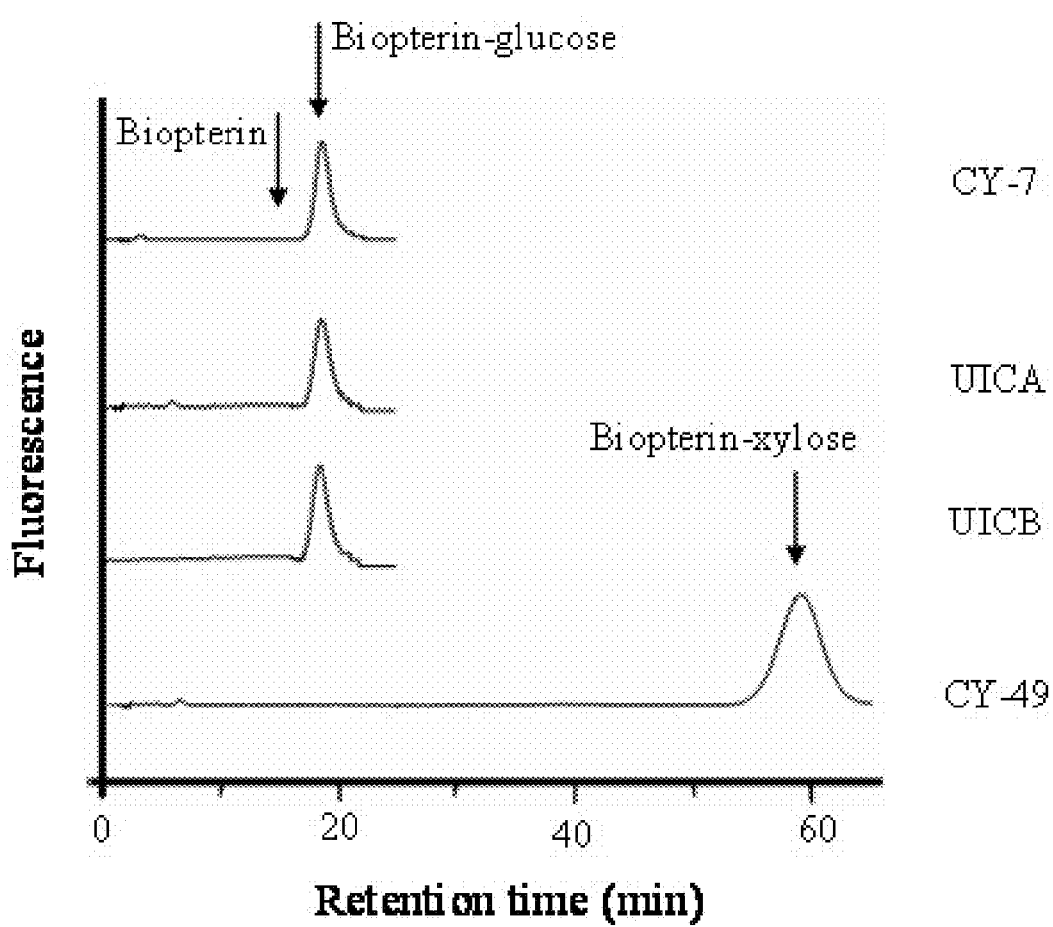
FIG. 10 shows the assay results of the recombinant proteins, i.e., HPLC chromatograms, which were obtained by incubating the purified recombinant proteins with the reaction mixture having tetrahydrobiopterin and UDP-glucose or UDP-xylose.

To isolate and purify the proteins identified from CY-7, CY-49, UICA and UICB, the genes encoding the proteins from each genomic DNA were amplified with PCR and then cloned into the pET expression vectors, which were expressed in E. coli. The resulting water-soluble recombinant proteins were purified through His-tag columns. FIG. 9 shows the result of electrophoresis on SDS-PAGE gel of the purified recombinant proteins.

(3) Identification of Protein Activity

The purified proteins were reacted with various substrates, i.e. UDP-glucose, UDP-galactose, UDP-xylose, UDP-glucuronic acid, UDP-galacturonic acid, UDP-N-acetylglucosamine, and UDP-N-acetylgalactosamine; and the products thereof were analyzed with HPLC. According to the HPLC analyses, it is found that all of the 4 proteins have an activity for binding sugar to tetrahydrobiopterin, namely the pteridine glycosyltransferase activity (see FIG. 10). Amongst them, the proteins isolated from CY-7, UICA and UICB represent an activity for binding glucose to tetrahydrobiopterin, while the protein isolated from CY-49 represents an activity for binding xylose to tetrahydrobiopterin. And also, there was no peak corresponding to biopterin in chromatograms, which means that all tetrahydrobiopterins was converted to its glycosylated product.

(4) Characterization of Enzyme Activity

Figure 11:
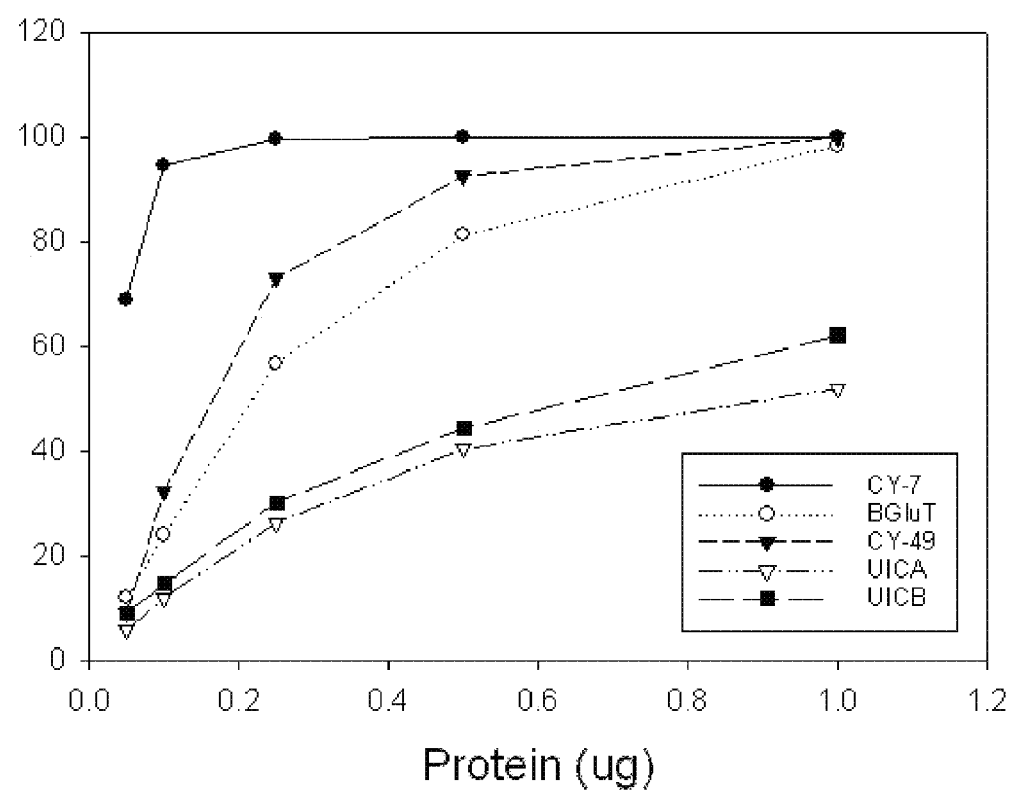
FIG. 11 shows comparative activities of pteridine glycosyltransferases according to increasing amounts of proteins.
Figure 12:
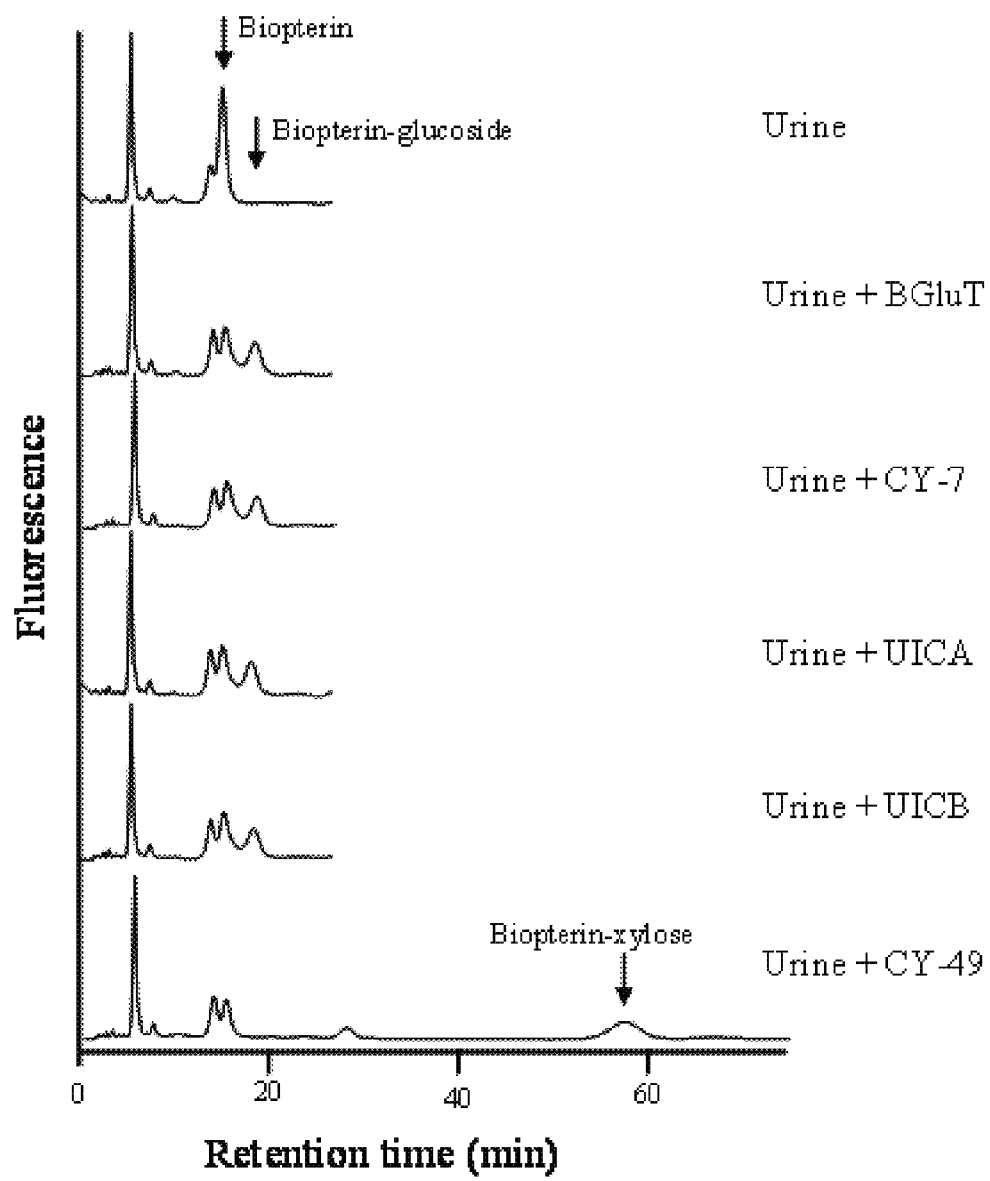
FIG. 12 shows HPLC chromatograms of the reaction mixtures of human urine incubated with or without pteridine glycosyltransferases. Tetrahydrobiopterin in the urine was converted to biopterin-glycosides, while oxidized forms remain as biopterin. The reaction mixture without enzyme treatment shows only biopterin peak.

Because the isolated proteins have only about 50% of identity with BGluT, the characteristics of the enzymatic activities thereof were compared with those of BGluT. FIG. 11 shows comparative analyses on production profiles of tetrahydrobiopterin (BH4)-glycoside products according to the amounts of proteins. Especially, the proteins obtained from CY-7 and CY-49 showed higher activities than BGluT. FIG. 12 is chromatograms representing the pteridine glycosyltransferase activities of the proteins, when human urine was used. The biopterin peak in the enzyme-free reaction mixture was decreased by the enzyme reaction; and the corresponding decreased amount was converted to the biopterin-glycoside product. The chromatograms of CY-7, UICA and UICB were very similar to that of BGluT. CY-49 having a UDP-xylose transfer activity showed the peak of biopterin-xylose, instead of biopterin-glucose. Accordingly, it was confirmed that UICA, UICB, CY-49, and CY-7, in addition to BGluT, can be used for simultaneously quantifying both tetrahydrobiopterin and its oxidized forms in a biological sample.

The proteins newly isolated in accordance with the present invention (i.e., proteins as set forth in SEQ ID NOs: 2 to 5) can convert all of tetrahydrobiopterin to its glycosylated product, like BGluT. Especially, the proteins show excellent pteridine glycosyltransferase activity, even though they have low identity (about 50%) with BGluT; and can selectively glycosylate tetrahydrobiopterin through enzyme reaction, which makes it possible to perform a simultaneous quantitative analysis of both tetrahydrobiopterin and its oxidized forms.

The invention claimed is:

1. A method for simultaneous quantitative analysis of both tetrahydrobiopterin and its oxidized forms in a sample, which comprises:
   (a) adding the sample comprising both tetrahydrobiopterin and its oxidized forms to an enzyme solution comprising
      (i) a protein having an amino acid sequence selected from the group consisting of SEQ ID NOs: 1, 2, 3, 4, and 5, and (ii) UDP-glucose or UDP-xylose, and then performing an enzymatic reaction;
   (b) oxidizing the reaction mixture obtained in Step (a) and then measuring each amount of biopterin and biopterin-glycoside product; and
   (c) obtaining an amount of tetrahydrobiopterin from the amount of biopterin-glycoside product obtained from Step (b), using a calibration curve between biopterin and biopterin-glycoside product.

2. The method according to claim 1, wherein the enzyme solution comprises 0.01 to 5 µg/100 µl of the protein selected from the group consisting of proteins as set forth in SEQ ID NOs: 1 to 5; 50 to 500 µM of UDP-glucose or UDP-xylose; 1 to 10 mM of a metal ion selected from the group consisting of $Mg^{2+}$, $Ca^{2+}$, and $Mn^{2+}$; and 0.04 to 0.4 w/w % of ascorbic acid, in phosphate-buffered saline or 10 to 100 mM of Tris-HCl buffer.

3. The method according to claim 1, wherein the enzyme solution comprises 0.5 to 1 µg/100 µl of the protein selected from the group consisting of proteins as set forth in SEQ ID NOs: 1 to 5; 250 to 500 µM of UDP-glucose or UDP-xylose; 10 mM of a metal ion selected from the group consisting of $Mg^{2+}$, $Ca^{2+}$, and $Mn^{2+}$; and 0.2 w/w % of ascorbic acid, in phosphate-buffered saline or 50 mM of Tris-HCl buffer.

4. The method according to claim 1, wherein the enzymatic reaction is performed at 37° C. for 5 to 20 minutes.

5. The method according to claim 1, wherein Step (b) is performed by oxidizing the reaction mixture obtained in Step (a) with an acidic iodine solution; and then measuring each amount of biopterin and biopterin-glycoside product by a single fluorometric high performance liquid chromatography.

6. The method according to claim 5, wherein the acidic iodine solution is a solution obtained by dissolving potassium iodide (KI) in a concentration of 1.8 to 2.2% and iodine ($I_2$) in a concentration of 0.9 to 1.1%, in 0.9 to 1.1 M of HCl solution.

* * * * *